United States Patent
Kobayashi et al.

(10) Patent No.: US 10,228,350 B2
(45) Date of Patent: Mar. 12, 2019

(54) SENSOR APPARATUS

(71) Applicant: KYOCERA CORPORATION, Kyoto (JP)

(72) Inventors: Kyohei Kobayashi, Otsu (JP); Yuji Kishida, Yokohama (JP)

(73) Assignee: KYOCERA CORPORATION, Kyoto (JP)

( * ) Notice: Subject to any disclaimer, the term of this patent is extended or adjusted under 35 U.S.C. 154(b) by 28 days.

(21) Appl. No.: 15/116,191

(22) PCT Filed: Jan. 27, 2015

(86) PCT No.: PCT/JP2015/052175
§ 371 (c)(1),
(2) Date: Aug. 2, 2016

(87) PCT Pub. No.: WO2015/115419
PCT Pub. Date: Aug. 6, 2015

(65) Prior Publication Data
US 2017/0016858 A1    Jan. 19, 2017

(30) Foreign Application Priority Data
Feb. 3, 2014 (JP) ................................. 2014-018561

(51) Int. Cl.
*G01N 15/06* (2006.01)
*G01N 33/00* (2006.01)
(Continued)

(52) U.S. Cl.
CPC ......... *G01N 29/022* (2013.01); *G01N 29/222* (2013.01); *G01N 29/2468* (2013.01);
(Continued)

(58) Field of Classification Search
CPC ......... G01N 15/06; G01N 33/00; G01N 33/48
(Continued)

(56) References Cited

U.S. PATENT DOCUMENTS 5,283,037 A    2/1994   Baer et al.
2007/0241637 A1*   10/2007   Kalantar-Zadeh ... G01N 29/022
                                                                310/313 D
(Continued)

FOREIGN PATENT DOCUMENTS

EP          542469 A1     5/1993
JP         05-240762 A    9/1993
(Continued)

OTHER PUBLICATIONS

Extended European Search Report dated Jul. 4, 2017, in corresponding European Patent Application No. 15743112.3.
(Continued)

*Primary Examiner* — Brian J. Sines
(74) *Attorney, Agent, or Firm* — Duane Morris LLP

(57) ABSTRACT

A sensor apparatus according to an embodiment of the present invention includes an element substrate, an element electrode located on an upper surface of the element substrate, an insulating member covering at least a part of the element electrode, and a detection part that includes an immobilizing film located on the upper surface of the element substrate or an upper surface of the insulating member, and performs a detection of a detection object contained in a specimen. A surface roughness of the immobilizing film is smaller than a surface roughness of the element electrode. In a sensor apparatus of other embodiment of the present invention, an amount of oxygen in a surface layer part of the immobilizing film is smaller than an amount of oxygen in a surface layer part of the element electrode.

14 Claims, 16 Drawing Sheets

(51) Int. Cl.
   *G01N 33/48* (2006.01)
   *G01N 29/02* (2006.01)
   *G01N 29/22* (2006.01)
   *G01N 29/24* (2006.01)
   *B01L 3/00* (2006.01)

(52) U.S. Cl.
   CPC ..... *B01L 3/5027* (2013.01); *B01L 2300/0645* (2013.01); *B01L 2300/0663* (2013.01); *B01L 2300/16* (2013.01); *G01N 2291/021* (2013.01); *G01N 2291/022* (2013.01); *G01N 2291/0255* (2013.01); *G01N 2291/0256* (2013.01); *G01N 2291/0257* (2013.01); *G01N 2291/0423* (2013.01); *G01N 2291/102* (2013.01)

(58) Field of Classification Search
   USPC ............... 422/50, 68.1, 82.01, 82.02; 436/43
   See application file for complete search history.

(56) References Cited

U.S. PATENT DOCUMENTS

2012/0073390 A1* 3/2012 Zaghloul ............. G01N 29/022
                                                         73/865

2014/0144237 A1* 5/2014 Komatsu ............. G01N 29/022
                                                         73/579

FOREIGN PATENT DOCUMENTS

| JP | 2561753 B1 | 12/1996 |
| JP | 2003-248001 A | 9/2003 |
| JP | 2007010378 A | 1/2007 |
| JP | 2007-139510 A | 6/2007 |
| WO | 2008/130327 A1 | 10/2008 |
| WO | WO 2010/146923 A1 | 12/2010 |
| WO | 2012/123749 A1 | 9/2012 |
| WO | WO 2013/147217 A1 | 10/2013 |

OTHER PUBLICATIONS

Lange, K. et al., "Surface acoustic wave biosensors: a review", Analytical and Bioanalytical Chemistry, Feb. 2008, 391(5):1509-1519.

International Search Report in International Application No. PCT/JP2015/052175, dated Apr. 28, 2015, in 2 pages.

PCT/JP2015/052175, dated Apr. 28, 2015, in 2 pages.

* cited by examiner

Fig.6
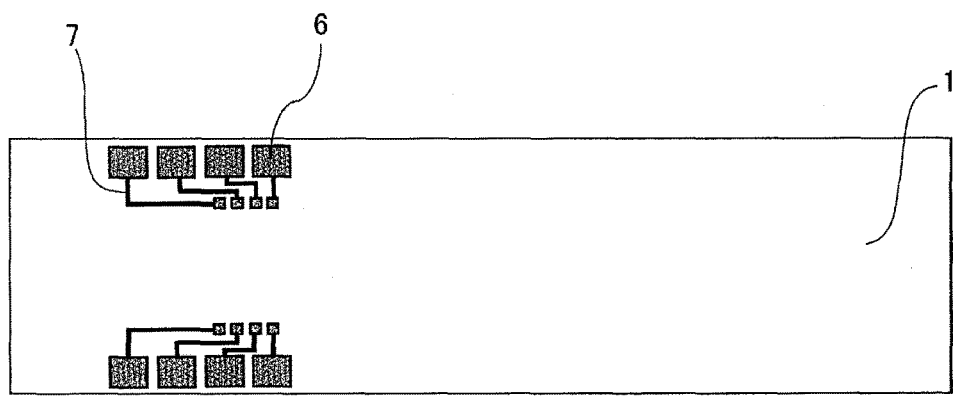
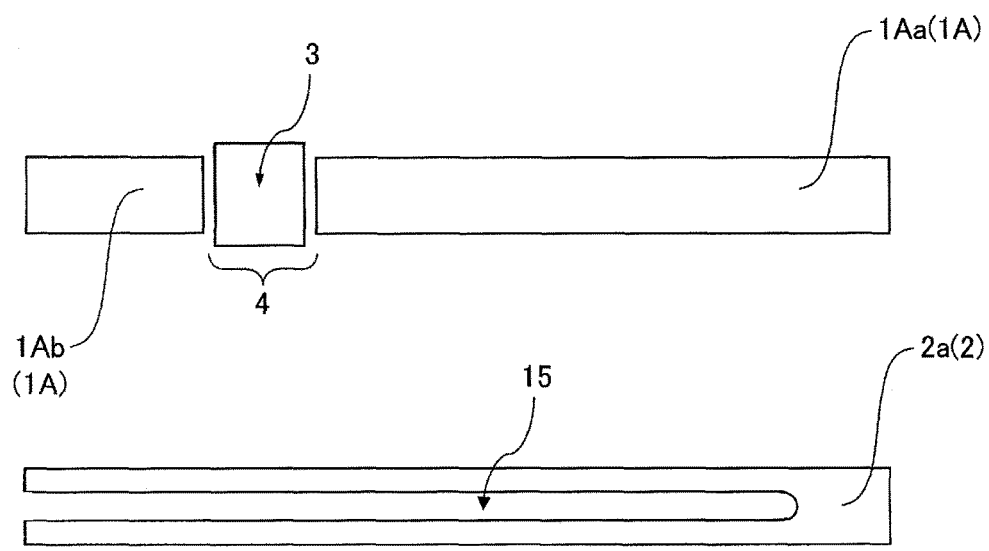
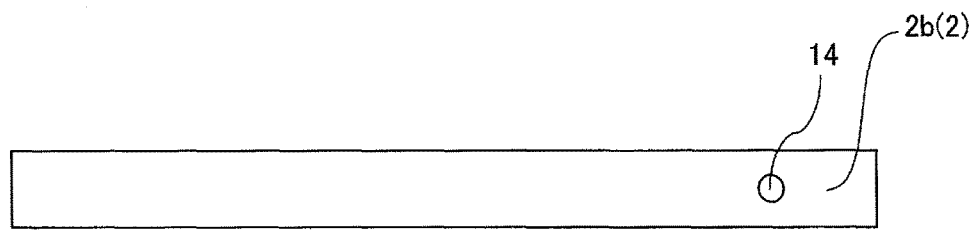

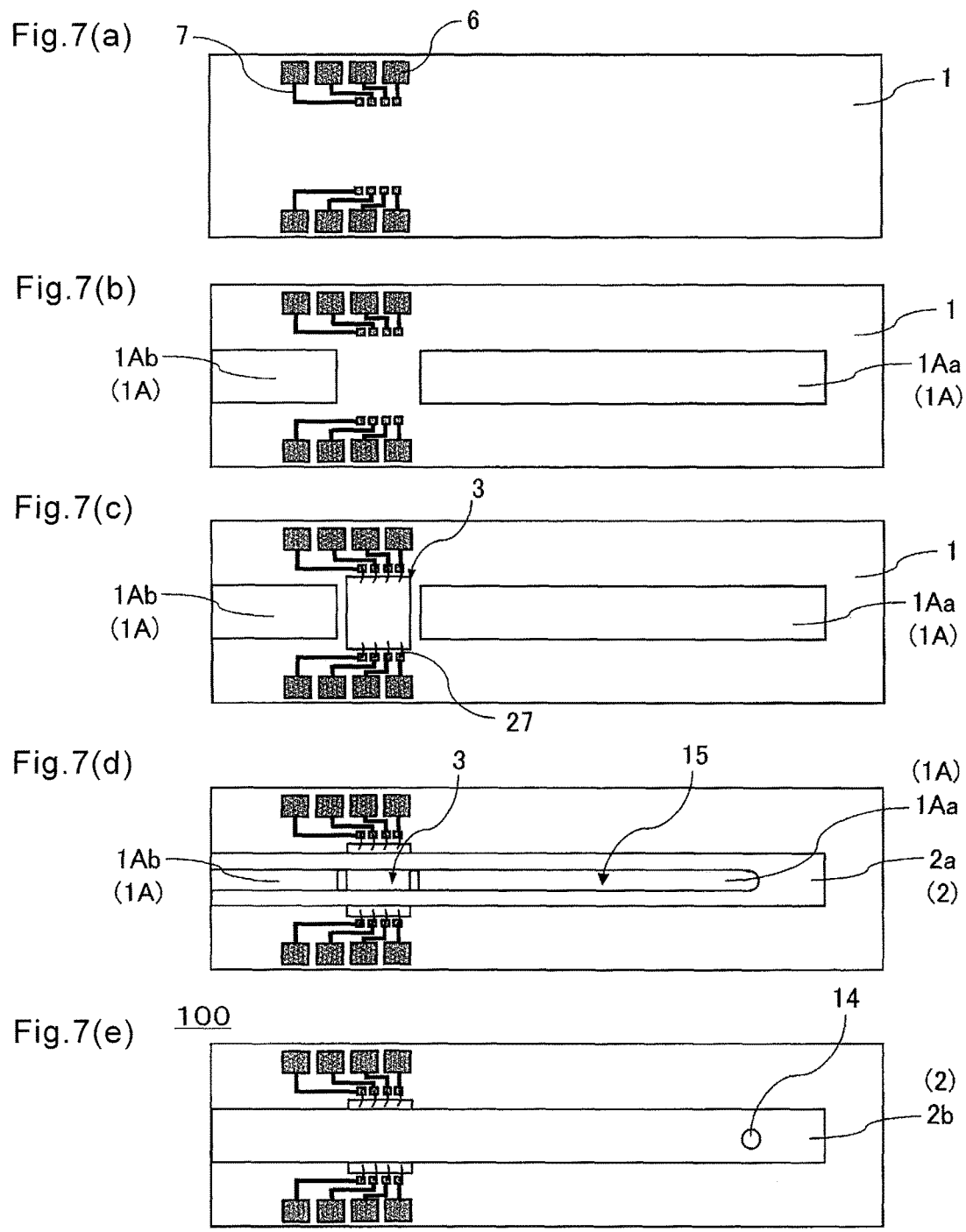

Fig.9(a)
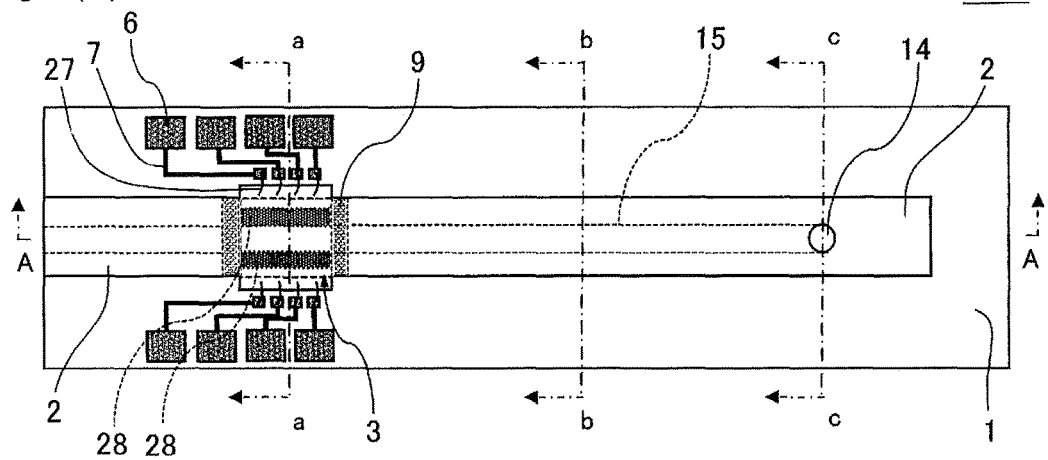
Fig.9(b)
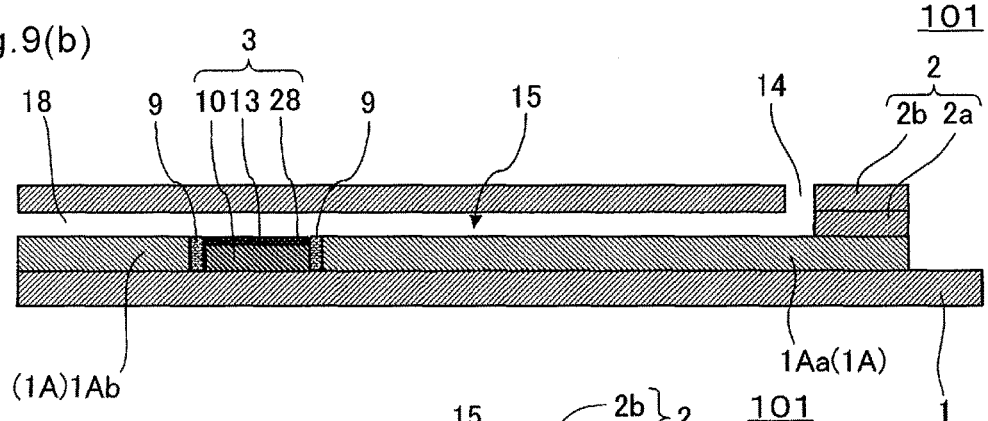
Fig.9(c)
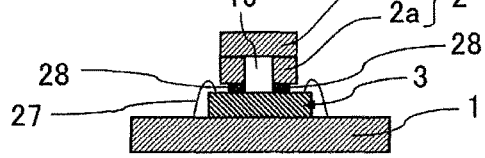
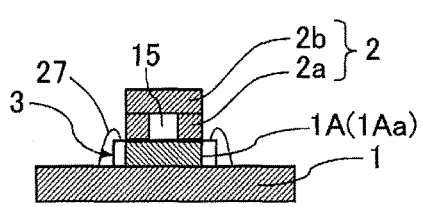
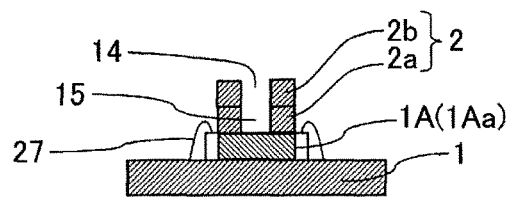

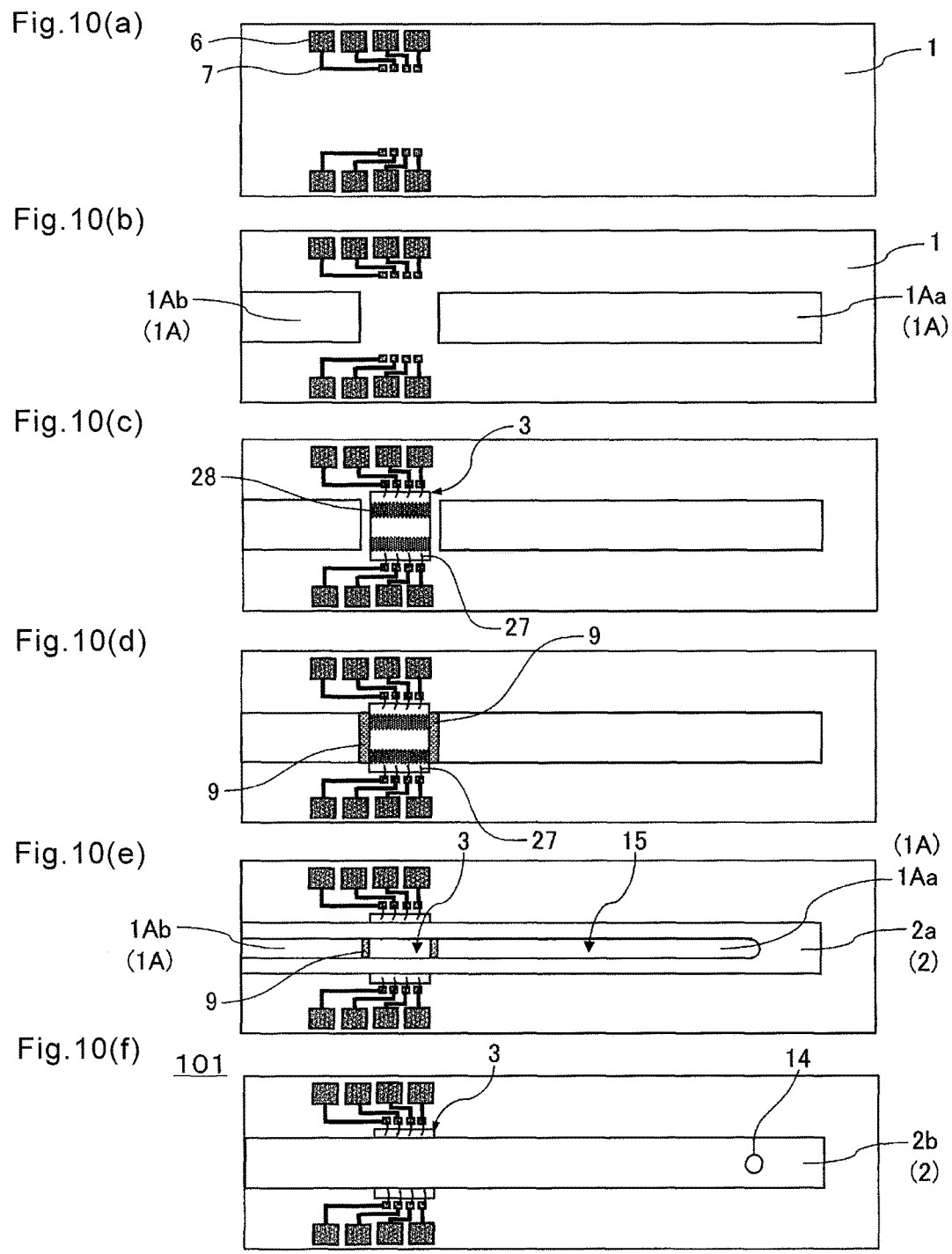

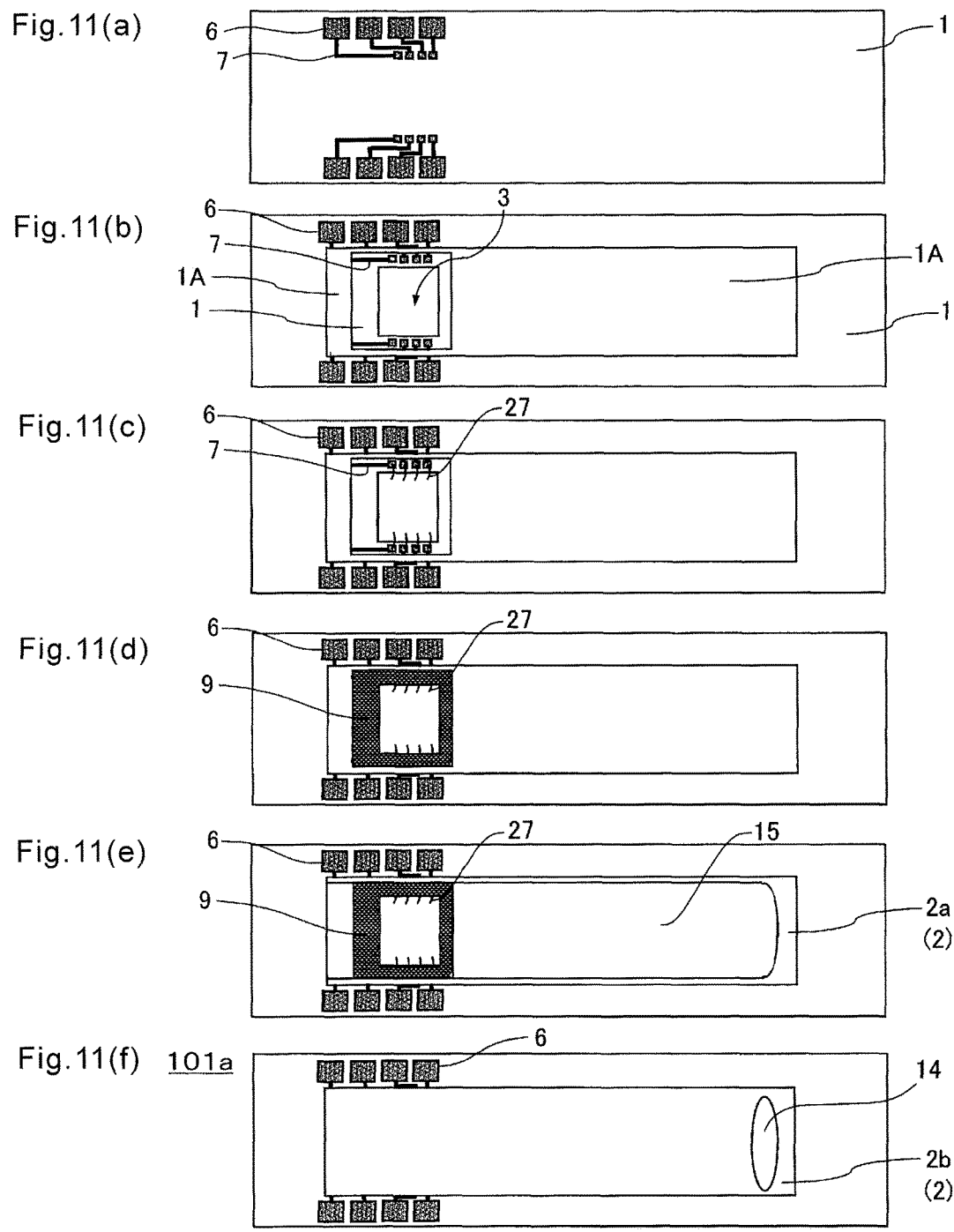

SENSOR APPARATUS

TECHNICAL FIELD

The present invention relates to a sensor apparatus capable of measuring nature of a specimen or ingredients contained in the specimen.

BACKGROUND ART

A sensor apparatus has been known which measures nature or ingredients of a specimen by using a detection element, such as a surface acoustic wave element (for example, refer to Japanese Unexamined Patent Publication No. 5-240762).

For example, the sensor apparatus using the surface acoustic wave element has, on a piezoelectric substrate, a detection part to be reacted with ingredients contained in a specimen. The sensor apparatus is configured to detect the nature or ingredients of the specimen by measuring a change of a surface acoustic wave after propagating along the detection part.

SUMMARY OF THE INVENTION

However, the detection part of the detection element, such as the surface acoustic wave element, has failed to have sufficient detection sensitivity or detection accuracy.

Hence, there has been a desire for a sensor apparatus capable of detecting a detection object with satisfactory sensitivity or satisfactory accuracy.

A sensor apparatus according to an embodiment of the present invention includes an element substrate, an element electrode located on an upper surface of the element substrate, an insulating member covering at least a part of the element electrode, and a detection part that includes an immobilizing film located on the upper surface of the element substrate or an upper surface of the insulating member, and performs a detection of a detection object contained in a specimen. A surface roughness of the immobilizing film is smaller than a surface roughness of the element electrode.

A sensor apparatus according to another embodiment of the present invention includes an element substrate, an element electrode located on an upper surface of the element substrate, an insulating member covering at least a part of the element electrode, and a detection part that includes an immobilizing film located on the upper surface of the element substrate or an upper surface of the insulating member, and performs a detection of a detection object contained in a specimen. An amount of oxygen in a surface layer part of the immobilizing film is smaller than an amount of oxygen in a surface layer part of the element electrode.

A sensor apparatus according to still another embodiment of the present invention includes an element substrate, an element electrode located on an upper surface of the element substrate, and a detection part that includes an immobilizing film located on the upper surface of the element substrate, and perform a detection of a detection object contained in a specimen. A surface roughness of the immobilizing film is smaller than a surface roughness of the element electrode. An amount of oxygen in a surface layer part of the immobilizing film is smaller than an amount of oxygen in a surface layer part of the element electrode.

With these sensor apparatuses, the surface roughness of the immobilizing film is smaller than the surface roughness of the element electrode, or the amount of oxygen in the surface layer part of the immobilizing film is smaller than the amount of oxygen in the surface layer part of the element electrode. It is therefore possible to effectively immobilize a component (for example, a functional group, an organic member, or a biomaterial) that contributes to the detection of the detection object contained in the specimen to a surface (upper surface) of the immobilizing film. It is consequently possible to detect the detection object with satisfactory sensitivity or accuracy.

BRIEF DESCRIPTION OF THE DRAWINGS

FIG. 6 is an exploded plan view of the sensor apparatus in FIG. 1;

FIG. 7 is a plan view showing a manufacturing process of the sensor apparatus in FIG. 1;

FIG. 9(a) is a plan view showing a modification of the sensor apparatus in FIG. 1, FIG. 9(b) is a sectional view thereof taken along a length direction, specifically, a sectional view along line A-A in FIG. 9(a), and FIG. 9(c) is a sectional view taken along a width direction, which is made up of sectional views respectively taken along line a-a, line b-b, and line c-c in FIG. 9(a) in order from the top on a paper surface;

FIG. 10 is a plan view showing a manufacturing process of the sensor apparatus in FIG. 9;

FIG. 11 is a diagram showing a modification of the sensor apparatus in FIG. 1, specifically a manufacturing process of the modification;

EMBODIMENTS FOR CARRYING OUT THE INVENTION

Figure 1A:
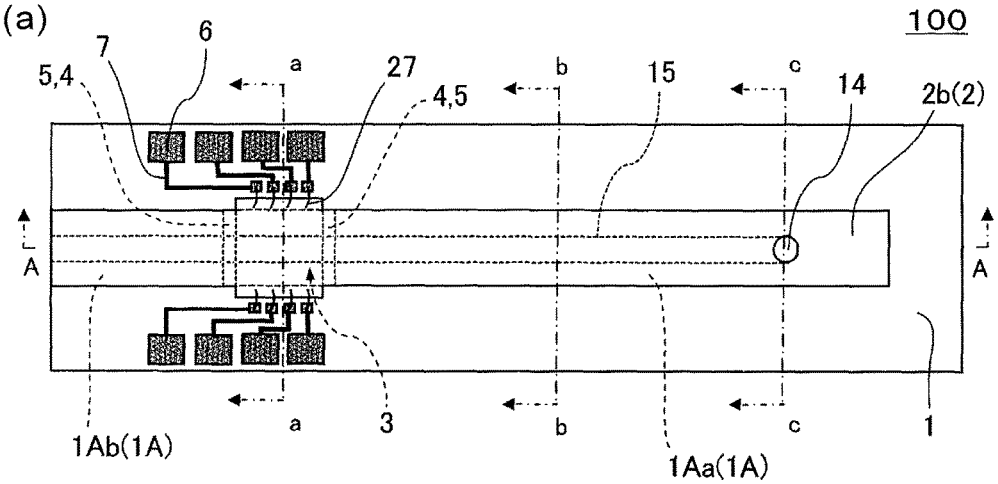
FIG. 1(a) is a plan view of a sensor apparatus according to a first embodiment of the present invention.

Sensor apparatuses respectively according to embodiments of the present invention are described in detail below with reference to the drawings by exemplifying a case where a specimen is in a liquid state (specimen liquid). Similar reference numerals are used to denote the same structural members in the drawings in the following description. Sizes of individual structural members and a distance between the members are schematically illustrated, and may be different from those of actual products thereof. In the following description, an upper surface of each of the members constituting the sensor apparatus, such as an element substrate, an insulating member, and an immobilizing film, is also referred to as a surface for the sake of convenience.

First Embodiment

A sensor apparatus 100 according to a first embodiment of the present invention is described with reference to FIGS. 1 to 7.

The sensor apparatus 100 of the present embodiment is mainly made up of a first cover member 1, and an intermediate cover member 1A, a second cover member 2, and a detection element 3 as shown in FIG. 1.

Figure 1B:
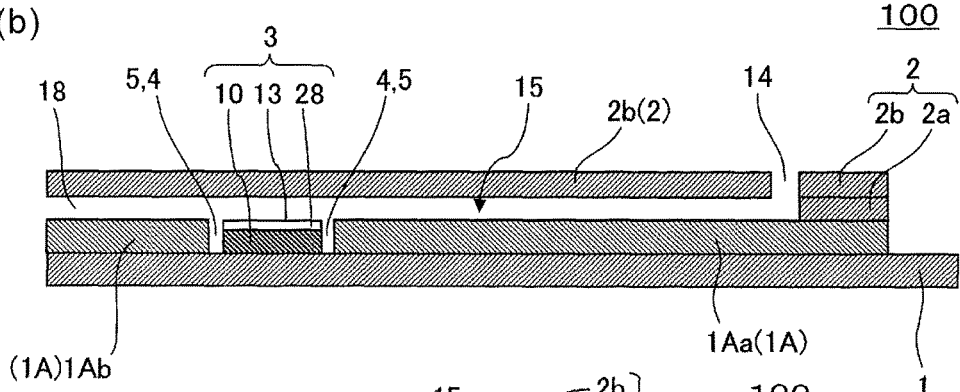
FIG. 1(b) is a sectional view taken along a length direction thereof, specifically, a sectional view taken along line A-A in FIG. 1(a)

Specifically, as shown in FIG. 1(b), the sensor apparatus 100 includes an inlet 14 that permits entrance of a specimen liquid, and a flow channel 15 that is continuous with the inlet 14 and extends to at least a detection part 13 while being surrounded by the intermediate cover member 1A and the second cover member 2. The inlet 14 is located on an upper surface of the intermediate cover member 1A and on a side surface of the second cover member 2 as shown in FIG. 1(b). Alternatively, the inlet 14 may penetrate the second cover member 2 in a thickness direction thereof as shown in FIG. 16(b).

In the sensor apparatus 100 of the present embodiment, the detection element 3 and the intermediate cover member 1A that constitutes at least a part of the flow channel 15 are disposed together on an upper surface of the first cover member 1. It is therefore possible to ensure the flow channel 15 for the specimen liquid which extends from the inlet 14 to the detection part 13 even when a thick detection element 3 is used. Accordingly, the specimen liquid sucked from the inlet 14 by capillary phenomenon or the like can be flown to the detection part 13. In other words, it is possible to provide the sensor apparatus 100 for simplifying a measurement operation which includes therein a suction mechanism for the specimen liquid while using the thick detection element 3. In the flow channel 15 for the specimen liquid, each of contact angles $\theta 1a$ and $\theta 2a$ of a surface of a member located upstream of the detection element 3 with respect to the specimen liquid is smaller than a contact angle $\theta 3$ of a surface of the detection element 3 (detection part 13) with respect to the specimen liquid. This achieves a smooth flow of the specimen liquid entering from the inlet 14, toward the detection element 3 (detection part 13) through the surface of the member located upstream.

(First Cover Member 1)

The first cover member 1 has a flat plate shape as shown in FIG. 1(b). A thickness of the first cover member 1 is, for example, 0.1-0.5 mm. The flat plate shape of the first cover member 1 is an approximately rectangular shape. A length of the first cover member 1 in a length direction thereof is, for example, 1-5 cm, and a length in a width direction thereof is, for example, 1-3 cm. As a material of the first cover member 1, it is possible to use, for example, paper, plastic, celluloid, ceramics, nonwoven fabric, and glass. It is preferable to use plastic in terms of both necessary strength and costs.

A terminal 6 and a wiring line 7 being laid from the terminal 6 to near the detection element 3 are disposed on the upper surface of the first cover member 1 as shown in FIG. 1(a). The terminal 6 is disposed on both sides in the width direction with respect to the detection element 3 on the upper surface of the first cover member 1. When the sensor apparatus 100 is measured with an external measuring device (not shown), the terminal 6 and the external measuring device are electrically connected to each other. The terminals 6 and the detection element 3 are electrically connected to one another via the wiring line 7 or the like. A signal from the external measuring device is to be inputted via the terminals 6 to the sensor apparatus 100, and a signal from the sensor apparatus 100 is to be outputted via the terminals 6 to the external measuring device.

(Intermediate Cover Member 1A)

In the present embodiment, the intermediate cover member 1A is located alongside the detection element 3 on the upper surface of the first cover member 1 as shown in FIGS. 1(a) and 1(b). The intermediate cover member 1A and the detection element 3 are located with a clearance interposed therebetween.

The intermediate cover member 1A is a member which includes a recess forming portion 4 on a tabular plate, and has a thickness of, for example, 0.1-0.5 mm. The thickness of the intermediate cover member 1A is preferably larger than a thickness of the detection element 3.

Figure 2A:
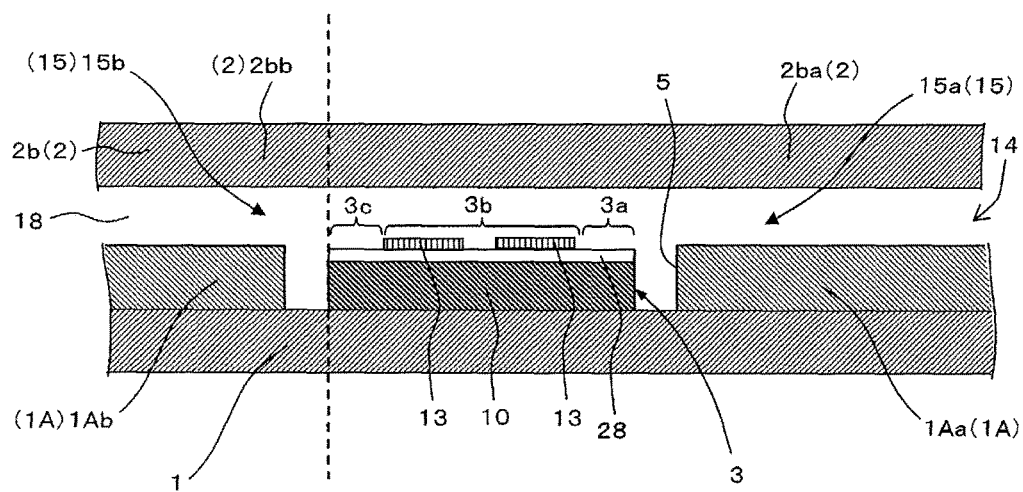
FIG. 2 is a partially enlarged sectional view of the sensor apparatus in FIG. 1.

In the present embodiment, the recess forming portion 4 is the portion that separates a first upstream portion 1Aa and a first downstream portion 1Ab as shown in FIGS. 1(a) and 1(b), and FIG. 6. By joining the intermediate cover member 1A provided with the recess forming portion 4 to the tabular first cover member 1, the first cover member 1 and the intermediate cover member 1A form an element accommodation recess 5 as shown in FIG. 2(a). That is, the upper surface of the first cover member 1 located inside the recess forming portion 4 becomes a bottom surface of the element accommodation recess 5, and an inner wall of the recess forming portion 4 becomes an inner wall of the element accommodation recess 5. In other words, the upper surface of the first cover member 1 which is exposed from the recess forming portion 4 becomes the bottom surface of the element accommodation recess 5, and the inner wall of the recess forming portion 4 becomes the inner wall of the element accommodation recess 5.

As a material of the intermediate cover member 1A, it is possible to use, for example, resins (containing plastic), paper, nonwoven fabric, and glass. More specifically, it is preferable to use resin materials, such as polyester resin, polyethylene resin, acrylic resin, and silicone resin. Alternatively, the material of the first cover member 1 and the material of the intermediate cover member 1A may differ from each other.

Additionally, the intermediate cover member 1A includes the first upstream portion 1Aa and the first downstream portion 1Ab in the present embodiment, and the detection element 3 is located between the first upstream portion 1Aa and the first downstream portion 1Ab in a top perspective (top view) in which the sensor apparatus 100 is seen through from the upper surface of the second cover member 2 as shown in FIG. 1(a). Owing to this, the specimen liquid flowing through the first upstream portion 1Aa of the flow channel 15 onto the detection element 3, the amount of which exceeds an amount necessary for measurement, flows toward the first downstream portion 1Ab, thus making it possible to supply a proper amount of the specimen liquid to the detection element 3.

(Second Cover Member 2)

Figure 1C:
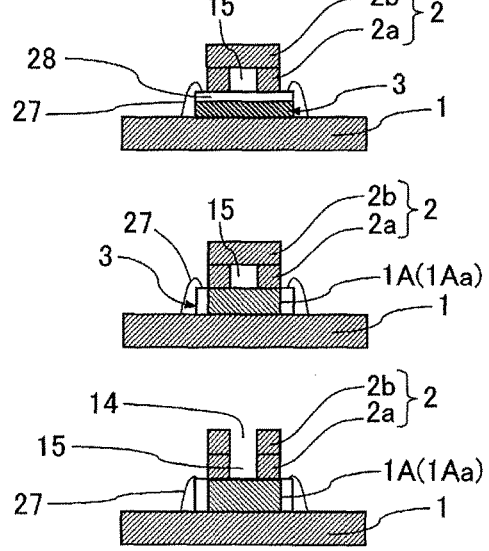
FIG. 1(c) is a sectional view taken along a width direction, which is made up of sectional views respectively taken along line a-a, line b-b, and line c-c in FIG. 1(a) in order from the top on a paper surface.

The second cover member 2 covers at least a part of the detection element 3 and is joined to the intermediate cover member 1A as shown in FIGS. 1(b) and 1(c). As a material of the second cover member 2, it is possible to use, for example, resin (containing plastic), paper, nonwoven fabric, and glass. More specifically, it is preferable to use resin materials, such as polyester resin, polyethylene resin, acrylic resin, and silicone resin. Alternatively, the material of the first cover member 1 and the material of the second cover member may be the same. This makes it possible to reduce deformation due to a difference between the thermal expansion coefficients of these cover members. The second cover member 2 may be joined only to the intermediate cover member 1A, or joined to both the first cover member 1 and the intermediate cover member 1A.

The second cover member 2 includes a third substrate 2a and a fourth substrate 2b.

The third substrate 2a is stuck to the upper surface of the intermediate cover member 1A. The third substrate 2a has a tabular shape and a thickness of, for example, 0.1-0.5 mm. The fourth substrate 2b is stuck to an upper surface of the third substrate 2a. The fourth substrate 2b has a tabular shape and a thickness of, for example, 0.1-0.5 mm. As shown in FIG. 6, a notch for forming the flow channel 15 is formed on the third substrate 2a. Therefore, as shown in FIG. 1(b), the flow channel 15 is to be formed on a lower surface of the second cover member 2 by joining the fourth substrate 2b to the third substrate 2a. The flow channel 15 extends from the inlet 14 to at least a region immediately above the detection part 13, and has a rectangular cross-sectional shape.

In the present embodiment, the third substrate 2a is not present at an end portion of the flow channel 15, and a clearance between the fourth substrate 2b and the intermediate cover member 1A functions as an exhaust hole 18 as shown in FIG. 1(b). The exhaust hole 18 is for exhausting air or the like in the flow channel 15 to the outside. The exhaust hole 18 may have any shape, such as a columnar or quadratic prism shape, as long as it is possible to release the air in the flow channel 15. However, an extremely large opening of the exhaust hole 18 increases an area where the specimen liquid staying in the flow channel 15 comes into contact with external air, thus facilitating evaporation of moisture in the specimen liquid. Consequently, the specimen liquid is susceptible to concentration change, resulting in deterioration of measurement accuracy. It is therefore preferable to make setting so that the opening of the exhaust hole 18 is not increased than necessary. Specifically, the setting is made so that a diameter of the columnar exhaust hole 18 is 1 mm or less, or one side of the quadratic prism shaped exhaust hole 18 is 1 mm or less. An inner wall of the exhaust hole 18 is hydrophobic, thereby suppressing the specimen liquid loaded in the flow channel 15 from leaking from the exhaust hole 18 to the outside.

All the first cover member 1, the intermediate cover member 1A, and the second cover member 2 may be formed of the same material. Accordingly, the coefficients of thermal expansion of these members can be made approximately equal to one another, thereby suppressing the deformation due to the difference in coefficient of thermal expansion that differs from member to member. A biomaterial 13b3 described later may be sometimes applied to the detection part 13. Some biomaterials are susceptible to alteration due to external light, such as ultraviolet light. In such cases, it is necessary to use an opaque one having light shielding properties as the material of the first cover member 1, the intermediate cover member 1A, and the second cover member 2. In the case where little or no alteration due to the external light occurs in the detection part 13, the second cover member 2 constituting the flow channel 15 may be formed of a nearly transparent material. This permits visual observation of a situation of the specimen liquid flowing through the flow channel 15.

(Detection Element 3)

As shown in FIG. 1(b), the detection element 3 includes an element substrate 10 located on the upper surface of the first cover member 1, and at least one detection part 13 which is located on the upper surface of the element substrate 10 or an upper surface of an insulating member 28 described later, and performs a detection of a detection object contained in the specimen liquid. Details of the detection element 3 are illustrated in FIGS. 2(b) and 3.

In the present embodiment, as shown in FIG. 3, an element electrode (electrode pattern) 29 is disposed on the upper surface of the element substrate 10, and the insulating member 28 is disposed so as to cover the element electrode 29. When an SAW element is used as the detection element 3, the element electrode 29 corresponds to an IDT (Interdigital Transducer) electrode and an extraction electrode. In the present embodiment, a first IDT electrode 11, a second IDT electrode 12, a first extraction electrode 19, and a second extraction electrode 20, which are described later, are disposed on the upper surface of the element substrate 10 as shown in FIG. 3.

Figure 2B:
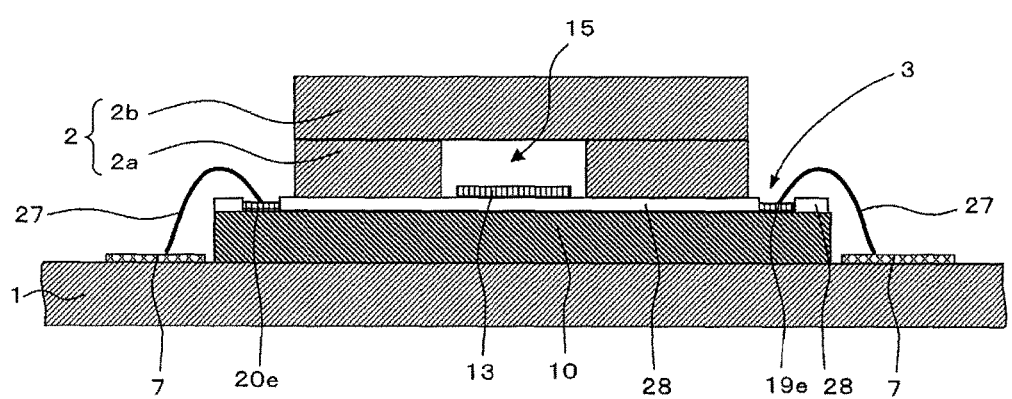

In the present embodiment, the second cover member 2 is secured, for example, onto the IDT electrodes 11 and 12 as shown in FIG. 2(b).

(Element Substrate 10)

The element substrate 10 is composed of a single crystal having piezoelectricity, such as lithium tantalate (LiTaO$_3$) single crystal, lithium niobate (LiNbO$_3$) single crystal, or quartz. A planar shape and dimensions of the element substrate 10 may be set appropriately. For example, a thickness of the element substrate 10 is 0.3-1.0 mm.

As the element electrode 29, the IDT electrodes 11 and 12 and the extraction electrodes 19 and 20 are sequentially described below.

(IDT Electrodes 11 and 12)

The first IDT electrode 11 is located on the upper surface of the element substrate 10, and includes a pair of interdigital electrodes as shown in FIG. 3. Each of the interdigital electrodes includes two bus bars facing each other, and a plurality of electrode fingers extending from each of the bus bars to another one. The pair of interdigital electrodes is disposed so that the electrode fingers mesh with each other. Similarly to the first IDT electrode 11, the second IDT electrode 12 is disposed on the upper surface of the element substrate 10, and includes a pair of interdigital electrodes. The first IDT electrode 11 and the second IDT electrode 12 shown in FIG. 3 constitute a transversal type IDT electrode.

The first IDT electrode 11 is for generating predetermined surface acoustic wave (SAW), and the second IDT electrode 12 is for receiving the SAW generated by the first IDT electrode 11. Here, the first IDT electrode 11 and the second IDT electrode 12 are disposed on the same straight line so that the second IDT electrode 12 can receive the SAW generated by the first IDT electrode 11. As described above, it is possible to design the frequency characteristics by using, as a parameter, the number of the electrode fingers between the first IDT electrode 11 and the second IDT electrode 12, the distance between the electrode fingers adjacent to each other, and a crossing width of the electrode fingers. As an SAW excited by the IDT electrode, there are ones having different vibrational modes. The detection element 3 of the present embodiment employs, for example, a vibrational mode of a transverse wave that is called SH wave (shear horizontal wave).

A frequency of the SAW is settable in a range of, for example, several megahertz (MHz) to several gigahertz (GHz). In particular, a range from several hundreds MHz to 2 GHz is practical and makes it possible to achieve downsizing of the detection element 3 as well as downsizing of the sensor apparatus 100.

Examples of materials of the first IDT electrode 11 and the second IDT electrode 12 include gold, aluminum, and an alloy of aluminum and copper (aluminum alloy). These electrodes may have a multilayer structure. When employing the multilayer structure, for example, a first layer may contain titanium or chromium, a second layer may contain gold, aluminum, or the aluminum alloy, and a third layer may contain titanium or chromium. In this case, the surface of titanium or chromium of the third layer may be oxidized, thereby making it possible to improve adhesion with $SiO_2$ that is the insulating member 28 described later. Examples of the multilayer structure include a three-layer structure (Ti/Au/Ti) having gold and titanium sequentially deposited on titanium, and a three-layer structure (Ti/Au/TiO$_2$) having gold and titanium oxide sequentially deposited on titanium. When employing the multilayer structure, an outermost layer of a plurality of layers may be composed of a different material different from an immobilizing film 13a described later. This is also true for the first extraction electrode 19 and the second extraction electrode 20 described later.

A thickness of each of the first IDT electrode 11 and the second IDT electrode 12 is settable to, for example, 30-300 nm. Transmission loss of the surface acoustic wave is reducible by setting the thickness of each of the first IDT electrode 11 and the second IDT electrode 12 to 30 nm or more. By setting the thickness of each of the first IDT electrode 11 and the second IDT electrode 12 to 300 nm or less, it is possible to suppress deterioration of detection sensitivity.

An elastic member (sound-absorbing member) for reducing SAW reflection may be disposed outside in an SAW propagation direction (width direction), specifically in the SAW propagation direction (width direction) of each of the first IDT electrode 11 and the second IDT electrode 12.

(Extraction Electrodes 19 and 20)

Figure 3A:
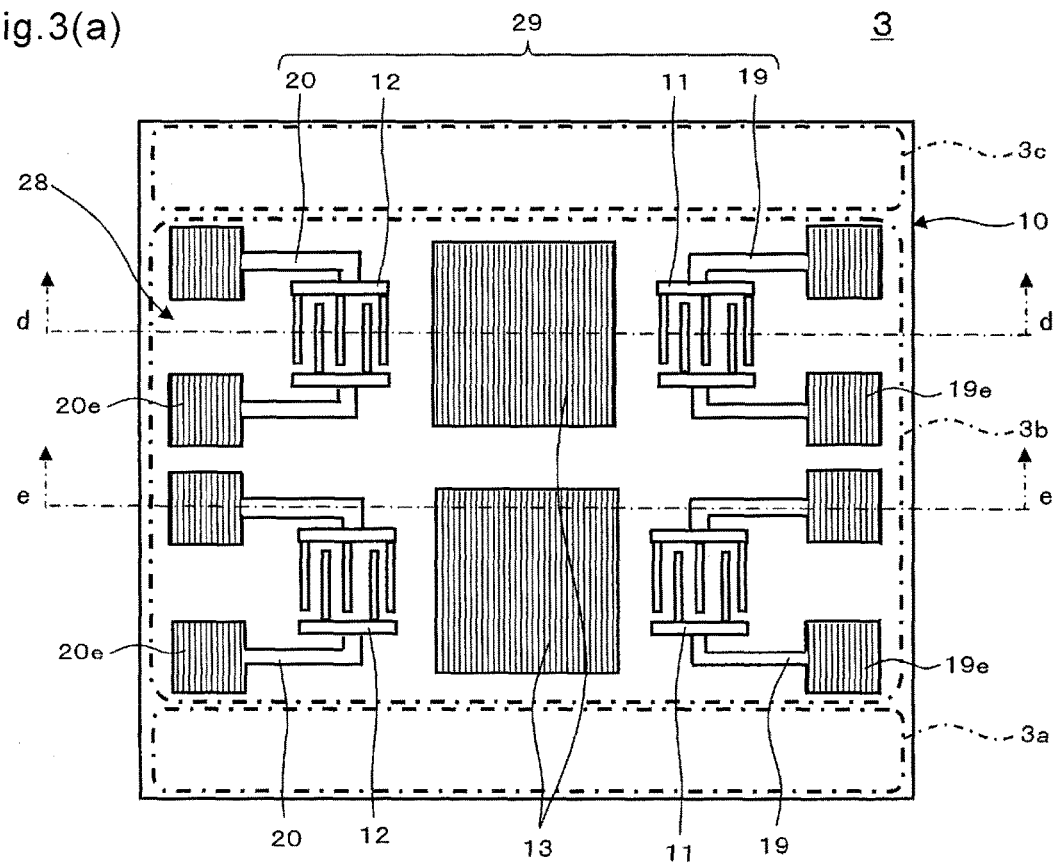
FIG. 3(a) is a plan view of a detection element of the sensor apparatus in FIG. 1.

The first extraction electrode 19 is connected to the first IDT electrode 11, and the second extraction electrode 20 is connected to the second IDT electrode 12 as shown in FIG. 3(a).

The first extraction electrode 19 is extracted from the first IDT electrode 11 toward the side opposite the detection part 13, and an end portion 19e of the first extraction electrode 19 is electrically connected to the wiring line 7 disposed on the first cover member 1. The second extraction electrode 20 is extracted from the second IDT electrode 12 toward the side opposite the detection part 13, and an end portion 20e of the second extraction electrode 20 is electrically connected to the wiring line 7. As shown in FIGS. 3(a) and 3(c), the end portion 19e of the first extraction electrode 19 and the end portion 20e of the second extraction electrode 20 are exposed without being covered with the insulating member 28 described later. In FIG. 3(a), a portion being exposed without being covered with the insulating member 28 is indicated by applying a pattern (vertical line hatching) to the portion.

As a material of the first extraction electrode 19 and the second extraction electrode 20, it is possible to use the same material as those of the first IDT electrode 11 and the second IDT electrode 12. When the end portion 19e of the first extraction electrode 19 and the end portion 20e of the second extraction electrode 20 are made into a multilayer structure, examples thereof include a two-layer structure having gold deposited on titanium (Ti/Au), a five-layer structure having gold, titanium, titanium, and gold deposited sequentially on titanium (Ti/Au/Ti/Ti/Au), and a five-layer structure having gold, titanium oxide, titanium, and gold deposited sequentially on titanium (Ti/Au/TiO$_2$/Ti/Au).

A thickness of each of the first extraction electrode 19 and the second extraction electrode 20 is settable to, for example, 30-300 nm. This ensures electrical continuity between the first IDT electrode 11 and the second IDT electrode 12. Alternatively, the thickness of each of the first extraction electrode 19 and the second extraction electrode 20 may be equal to those of the first IDT electrode 11 and the second IDT electrode 12. With this configuration, a manufacturing process can be simplified by manufacturing the extraction electrodes and the IDT electrodes in the same process, and the adhesion with the insulating member 28 can be made uniform because no difference in level occurs on electrode surfaces at connection parts between the extraction electrodes and the IDT electrodes. It is consequently possible to suppress, for example, occurrence of cracks in the insulating member 28 upon application of stress.

(Insulating Member 28)

The insulating member 28 contributes to suppressing oxidation of element electrodes (such as the IDT electrodes 11 and 12, and the extraction electrodes 19 and 20) 29, and covers at least a part of the element electrodes 29 as shown in FIG. 3.

Figure 3B:
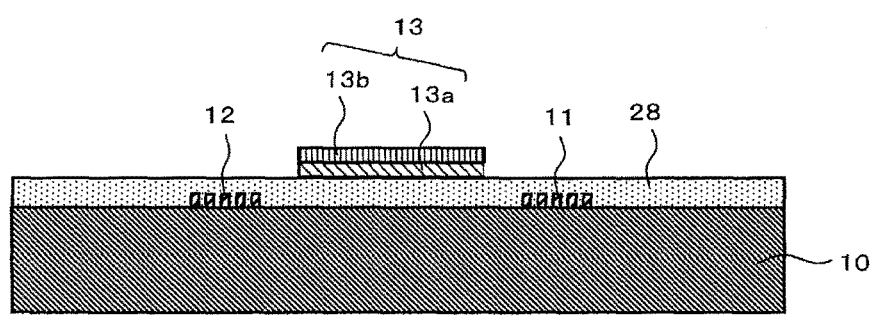
FIG. 3(b) is a sectional view thereof taken along line d-d in FIG. 3(a)
Figure 3C:
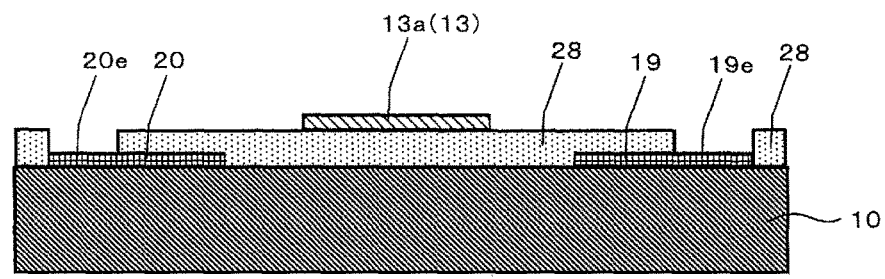
FIG. 3(c) is a sectional view taken along line e-e in FIG. 3(a)

In the present embodiment, the insulating member 28 covers the first IDT electrode 11 and the second IDT electrode 12 as shown in FIG. 3(b). The insulating member 28 also covers the first extraction electrode 19 and the second extraction electrode 20. However, as shown in FIGS. 3(a) and 3(c), each of the end portion 19e of the first extraction electrode 19 and the end portion 20e of the second extraction electrode 20 includes a region at least part of which is not covered with the insulating member 28. As shown in FIG. 2(b), the uncovered region and the wiring line 7 are electrically connected to each other by using a thin metallic wire (conducting wire) 27. Alternatively, the insulating member 28 may be formed so as to cover the thin metallic wire 27 and the wiring line 7.

Examples of the material of the insulating member 28 includes silicon oxide ($SiO_2$), aluminum oxide, zinc oxide, titanium oxide, silicon nitride, and silicon. The insulating member 28 preferably includes $SiO_2$ among these exemplified materials.

A thickness of the insulating member 28 is settable to, for example, 10-2000 nm. By setting the thickness of the insulating member 28 to 10 nm or more, it is possible to have excellent temperature characteristics and ensure sufficient insulating properties against the IDT electrodes 11 and 12, and the like. By setting the thickness of the insulating member 28 to 2000 nm or less, it is possible to suppress deterioration of detection sensitivity and have excellent temperature characteristics.

FIG. 4 is a diagram showing a modification of the sensor apparatus in FIG. 1, and is a sectional view corresponding to FIG. 3(b).

Figure 4A:
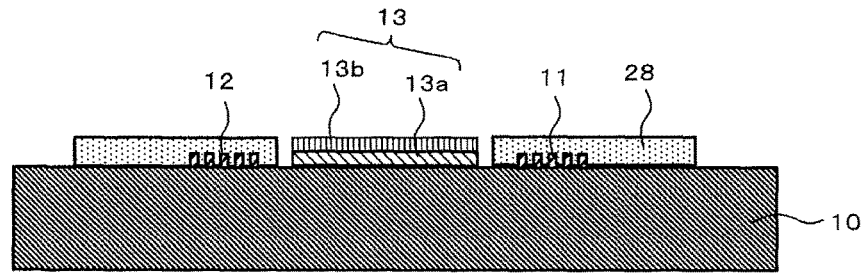
FIG. 4 is a diagram showing a modification of the sensor apparatus in FIG. 1, specifically a sectional view corresponding to FIG. 3(b)

In FIG. 4(a), the insulating member 28 covers only a part of the element substrate 10. The detection part 13 is formed at a region of the surface (upper surface) of the element substrate 10 which is not covered with the insulating member 28. With this configuration, the amplitude of surface acoustic wave becomes large in the vicinity of the surface of the element substrate 10 in the region not covered with the insulating member 28, and the surface of the element substrate 10 and a reaction part 13b described later are close to each other in the region, thereby making it possible to improve the detection sensitivity.

Figure 4B:
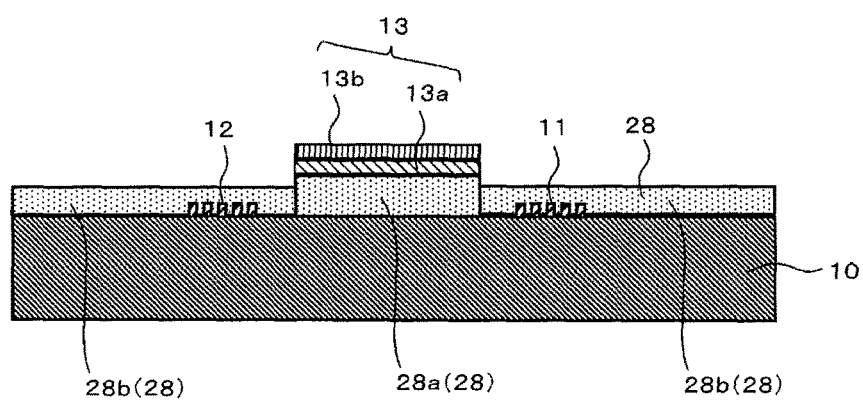

In FIG. 4(b), the insulating member 28 covers the element substrate 10. However, a portion of the region covered with the insulating member 28, on which the detection part 13 is formed, has a larger thickness than other portions. In other words, on the upper surface of the insulating member 28, an outer peripheral portion 28b being continuous with a covered portion 28a covered with the immobilizing film 13a described later is lower than the covered portion 28a in a sectional view shown in FIG. 4(b). With this configuration, for example, when performing a liquid manipulation, such as immobilization of the reaction part 13b against the surface of the immobilizing film 13a described later, it is easy to perform the liquid manipulation by separating the detection part 13 and other regions. For example, by inserting a tool having a through hole so as to surround the detection part 13 with the through hole, it is easy to perform positioning of the tool.

Figure 4C:
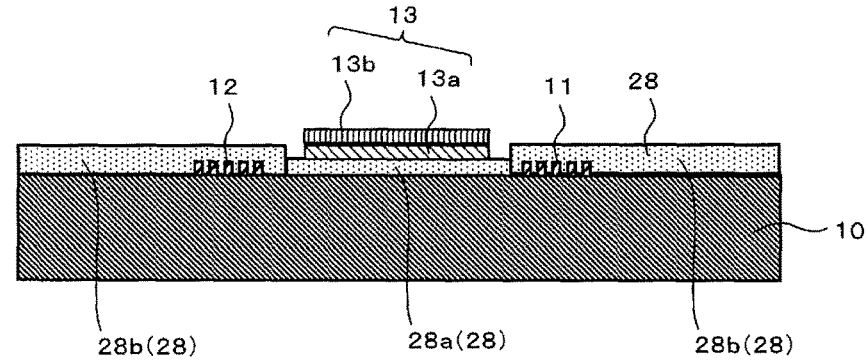

In FIG. 4(c), the insulating member 28 covers the element substrate 10. However, a portion of the region covered with the insulating member 28, on which the detection part 13 is formed, has a smaller thickness than other portions. In other words, on the upper surface of the insulating member 28, the outer peripheral portion 28b being continuous with the covered portion 28a covered with the immobilizing film 13a is higher than the covered portion 28a in a sectional view shown in FIG. 4(c). This configuration produces effects similar to those produced by the modification in FIG. 4(a), and also achieves the ease of positioning of the tool as in the modification in FIG. 4(b). The covered portion 28a in the present modification includes, besides the portion of the upper surface of the insulting member 28 which is covered with the immobilizing film 13a, a circumferential portion of the above-mentioned portion.

(Detection Part 13)

As shown in FIG. 3, the detection part 13 is for detecting a detection object contained in the specimen liquid, and is located between the first IDT electrode 11 and the second IDT electrode 12 on the upper surface (surface) of the element substrate 10 or the upper surface of the insulating member 28. The detection part 13 includes the immobilizing film 13a located on the upper surface (surface) of the element substrate 10 or the upper surface (surface) of the insulating member 28, and the reaction part 13b located on the upper surface of the immobilizing film 13a.

(Immobilizing Film 13a)

The immobilizing film 13a is located on the upper surface (surface) of the element substrate 10 or the upper surface (surface) of the insulating member 28, and is for immobilizing the reaction part 13b on the upper surface (surface) thereof. In the present embodiment, the detection part 13 is located between the first IDT electrode 11 and the second IDT electrode 12 as described above, and accordingly the immobilizing film 13a is also located between the first IDT electrode 11 and the second IDT electrode 12. More specifically, the immobilizing film 13a is located between the first IDT electrode 11 and the second IDT electrode 12 in the top perspective in which the sensor apparatus 100 is seen through from the upper surface of the second cover member 2.

For example, metal is usable as a material of the immobilizing film 13a. The immobilizing film 13a may include the same material as the element electrode 29, such as the first IDT electrode 11 and the second IDT electrode 12. The element electrode 29 and the immobilizing film 13a may include Au. As a material of the immobilizing film 13a, other metal materials (such as platinum, silver, palladium, and alloys thereof) are usable in addition to the same material as the first IDT electrode 11 and the second IDT electrode 12. Alternatively, the immobilizing film 13a may have a multilayer structure. When the immobilizing film 13a is made into the multilayer structure, it is possible to employ a two-layer structure made up of chromium or titanium, and gold deposited on chromium (or titanium), and a three-layer structure further having titanium oxide deposited on gold. Examples of the multilayer structure includes a two-layer structure having gold deposited on titanium (Ti/Au), and a three-layer structure having gold and titanium oxide deposited sequentially on titanium (Ti/Au/TiO$_2$). In particular, with the two-layer structure (Ti/Au) having gold deposited on titanium, it is easy to make setting so that an amount of oxygen in a surface layer part of the immobilizing film 13a described later is smaller than an amount of oxygen in a surface layer part of the element electrode 29. Besides the above-mentioned ones, for example, SiO$_2$ is usable as a material of the immobilizing film 13a.

A thickness of the immobilizing film 13a is settable to, for example, 30-300 nm. By setting the thickness of the immobilizing film 13a to 30 nm or more, it is possible to suppress deterioration of the detection sensitivity. The transmission loss of surface acoustic wave can be reduced by setting the thickness of the immobilizing film 13a to 300 nm or less. In the configuration shown in FIG. 3 or 4(b), the thickness of the immobilizing film 13a is preferably set to be smaller than the thickness of the element electrode (such as IDT electrodes 11 and 12, and the extraction electrodes 19 and 20) 29. This contributes to reducing the transmission loss of surface acoustic wave. In the configuration shown in FIG. 4(a) or 4(c), the thickness of the immobilizing film 13a is preferably set to be equal to or larger than the thickness of the element electrode (such as IDT electrodes 11 and 12, and the extraction electrodes 19 and 20) 29. This contributes to improving the detection sensitivity.

A surface roughness of the immobilizing film 13a is settable to be smaller than a surface roughness of the element electrode 29. For example, setting may be made so that the surface roughness of the immobilizing film 13a is 0.1-5 nm and the surface roughness of the element electrode 29 is in the same range as the surface roughness of the immobilizing film 13a while the surface roughness of the immobilizing film 13a is made smaller. This makes it possible for an organic member 13h2 described later to be bound to the surface of the immobilizing film 13a with high uniformity. It is therefore possible to suppress a biomaterial 13b3 described later from subsequently unintentionally binding to the surface of the immobilizing film 13a. It is also possible to improve stability of the amount of immobilization of the biomaterial 13b3 onto the organic member 13b2.

By setting the surface roughness of the immobilizing film 13a to be smaller than the surface roughness of the element electrode 29, a large amount of the biomaterial 13b2 can be formed with high uniformity even when the biomaterial 13b3 is bound to the surface of the immobilizing film 13a without using the organic member 13b2.

Thus, with the sensor apparatus 100 of the present embodiment, the surface roughness of the immobilizing film 13a is smaller than the surface roughness of the element electrode 29. Therefore, the component that contributes to the detection of the detection object contained in the specimen liquid can of be immobilized while suppressing non-specific adsorption of materials other than the detection object contained in the specimen liquid with respect to the surface (upper surface) of the immobilizing film 13a, thereby making it possible to detect the detection object with satisfactory accuracy. Additionally, the surface roughness of the element electrode 29 has a certain degree of size, thereby achieving excellent adhesion to the insulating member 28 to be formed on the surface of the element electrode 29. The surface roughness of the immobilizing film 13a is preferably smaller than the surface roughness of each of the first IDT electrode 11 and the second IDT electrode 12.

The surface roughness is measurable with, for example, a transmission electron microscope (TEM). For example, a cross section including an object surface to be subjected to surface roughness measurement needs to be observed with the TEM to measure a peak-valley value of the object surface. Preferably, the observation with the TEM is carried out with respect to optionally selected 2 to 10 locations in the cross section, and an average value thereof is taken as the peak-valley value. For example, when the reaction part 13b described later is not immobilized onto the surface of the immobilizing film 13a and the surface of the immobilizing film 13a is exposed, an arithmetic average roughness Ra may be employed as a surface roughness. The surface roughness Ra is measurable with, for example, a scanning probe microscope (SPM). For example, a single crystal Si rotational probe whose front end diameter corresponds to 10 nm needs to scan the object surface in tapping mode under conditions that a scanning range is 1-3 µm□ and a scanning speed is 0.702 Hz. In foregoing measuring conditions, for example, the surface roughness of the immobilizing film 13a needs to have an average value of approximately 1.7 nm, and the surface roughness of the element electrode 29 needs to have an average value of approximately 2.0 nm.

The amount of oxygen in the surface layer part of the immobilizing film 13a can be set smaller than the amount of oxygen in the surface layer part of the element electrode 29. For example, the amount of oxygen in the surface layer part of the immobilizing film 13a needs to be set to less than 11 atomic %, and the amount of oxygen in the surface layer part of the element electrode 29 needs to be set to 17-20 atomic %. This achieves effective binding of a functional group 13b1, such as SH group (thiol group) described later, to the surface of the immobilizing film 13a. Accordingly, the large amount of organic member 13b2 described later is bindable via the functional group 13b1 with high uniformity. It is therefore possible to suppress the biomaterial 13b3 described later from subsequently unintentionally binding to the surface of the immobilizing film 13a. It is also possible to improve stability of the amount of immobilization of the biomaterial 13b3 onto the organic member 13b2. By setting the amount of oxygen in the surface layer part of the immobilizing film 13a to be smaller than the amount of oxygen in the surface layer part of the element electrode 29, a large amount of the biomaterial 13b3 can be formed with high uniformity even when the biomaterial 13b3 is bound to the surface of the immobilizing film 13a via the functional group 13b1 without using the organic member 13b2.

Thus, with the sensor apparatus 100 of the present embodiment, the amount of oxygen in the surface layer part of the immobilizing film 13a is smaller than the amount of oxygen in the surface layer part of the element electrode 29. Therefore, the component that contributes to the detection of the detection object contained in the specimen liquid can effectively be immobilized, thus making it possible to detect the detection object with satisfactory accuracy. The amount of oxygen in the surface layer part of the immobilizing film 13a is preferably smaller than the amount of oxygen in the surface layer part of each of the first IDT electrode 11 and the second IDT electrode 12.

The amount of oxygen in the surface layer part of each of the immobilizing film 13a and the element electrode 29 is measurable with, for example, electron energy loss spectroscopy (EELS). For example, when the immobilizing film 13a is gold (Au), a binding state of Au in a cross section including a region near the surface of the immobilizing film 13a needs to be measured with EELS. The amount of oxygen in the surface layer part of each of the immobilizing film 13a and the element electrode 29 is also measurable with X-ray photoelectron spectroscopy (XPS). In either of the measurement methods, the amount of oxygen needs to be measured by taking, as the surface layer part, a depth of approximately 2 nm from the surface of the immobilizing film 13a. For example, kinetic energy of electrons ejected from the surface of needs to be detected by irradiating AlKα ray that is x-ray source (1486.6 eV, 24.8 W, 15 kV) to a region of an approximately 100 µmϕ on the surface of the immobilizing film 13a. On that occasion, pass energy of a detector needs to set to approximately 224 eV. For example, when the immobilizing film 13a is gold (Au), in a gold (Au) surface analysis with XPS, Au 4 f signal and O1s signal respectively normally appear in the vicinity of binding energy 84 eV and 530 eV, and the amount of oxygen in the surface layer part can be quantified from signal intensity of O1s. A situation where gold is oxidized into gold oxide ($Au_2O_3$) is observable by a chemical shift of approximately +1.5 to 2 eV that occurs in Au 4 f. An amount thereof can be quantified from a calibration curve of $Au_2O_3$ of a standard sample. The signal of O1s caused by OH group (hydroxyl group) adsorbed on the surface appears at binding energy (approximately 531 eV) that is approximately 1 eV higher. Therefore, the oxygen of OH group adsorbed on the surface and the oxygen in the surface layer part of the immobilizing film 13a (gold) are distinguishable.

(Reaction Part 13b)

Figure 5:
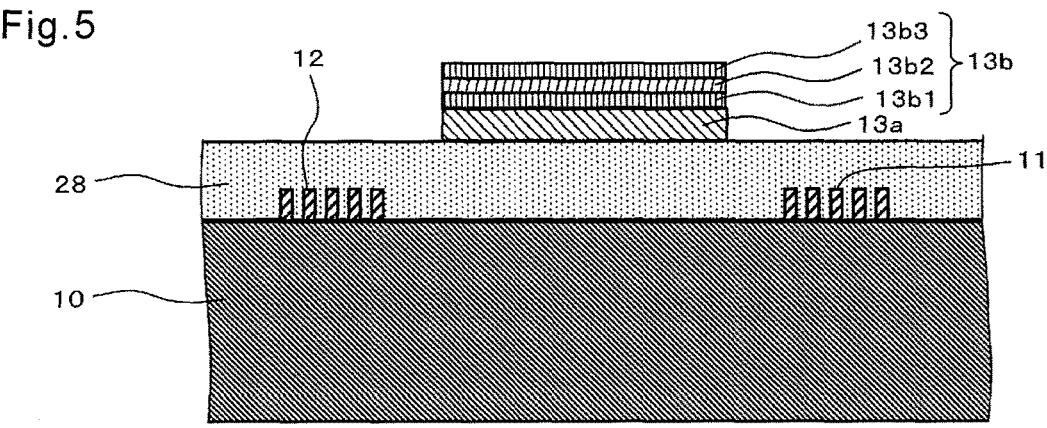
FIG. 5 is a partially enlarged sectional view of the sensor apparatus shown in FIG. 3(b)

The reaction part 13b is a portion that causes a chemical reaction with the detection object in the specimen liquid, and is located on the surface (upper surface) of the immobilizing film 13a as shown in FIG. 5. Examples of the reaction part 13b includes a structure that the biomaterial 13b3 is immobilized via the functional group 13b1 described later on the surface of the immobilizing film 13a, and a structure that the biomaterial 13b3 is immobilized via the functional group 13b1 and the organic member 13b2 as shown in FIG. 5. In other words, the functional group 13b1 has a role in immobilizing the biomaterial 13b3 directly, or via the organic member 13b2 or the like, to the surface of the immobilizing film 13a. In the reaction part 13b having the foregoing structure, for example, a specific detection object in the specimen liquid is bound to the biomaterial 13b3, such as an aptamer corresponding to the detection object, due to a contact with the specimen liquid.

The functional group 13b1 is, for example, SH group (thiol group). Besides that, there are, for example, amino group, carboxyl group, maleimide group, sulfide group, disulfide group, aldehyde group, azide group, N-hydroxysuccinimide group, epoxy group, carbonyldiimidazole group, isocyanate group, hydroxyl group, hydrazide group, vinyl group, tosyl group, tresyl group, succinimide group, sulfonated succinimide group, and biotin group. The reaction part 13b preferably includes a thiol group among the exemplified functional groups 13b1, which is bound to the upper surface of the immobilizing film 13a. The reaction part 13b preferably further includes the organic member 13b2 being bound to a thiol group.

As the organic member 13b2, there are, for example, dextran, agarose, alginic acid, carrageenan, sugars similar to these, and derivatives of any one of these; polyvinyl alcohol, polyacryl amide, polyacrylic acid, oligoethylene glycol, polyethylene glycol, cellulose, and organic polymers similar to these; and self-assembled monolayers (SAM films). As the self-assembled monolayer, there are, for example, ones which incorporates straight-chain or branched hydrocarbon chains including a carbon length of approximately 1-400. The hydrocarbon chains can incorporate alkyl group, aryl group, alkenyl group, alkynyl group, cycloalkyl group, alkaryl group, aralkyl group, and optional combinations of these. There are, for example, $HS-(CH_2)_n-NH^{3+}Cl^-$, and $HS-(CH_2)_n-COOH$. Alkyl chains having a carbon length of n=approximately 3 to 30 are preferable.

The organic member 13b2 can be made into a structure that a small molecular weight material and a large molecular weight material are laminated sequentially from the immobilizing film 13a side. The small molecular weight material is capable of covering the surface of the immobilizing film 13a more uniformly and densely, and the large molecular weight material is capable of more reducing the non-specific binding. Hence, the combination of these leads to a base suitable for immobilization of the biomaterial 13b3. When the organic member 13b2 is made up of a plurality of layers, it is possible to use the self-assembled monolayer (SAM film) as a lowermost layer, thereby covering the surface of the immobilizing film 13a at high density.

The biomaterial 13b3 has molecular recognition ability to bind to a specific material with selectivity, and preferably includes at least one kind selected from among peptide, protein (including antibody), and nucleic acid (including aptamer). The biomaterial 13b3 is immobilized above the immobilizing film 13a. To be specific, the biomaterial 13b3 can be immobilized to the surface of the immobilizing film 13a via the functional group 13b1 as described above, or via the organic member 13b2 including a homobifunctional group or heterobifunctional group at both ends thereof. For example, the biomaterial 13b3, such as aptamer, needs to be immobilized to the upper surface (upper part) of the organic member 13b2 covering almost the entire region of the surface of the immobilizing film 13a. Alternatively, the biomaterial 13b3 needs to be immobilized to the surface of the immobilizing film 13a via the functional group 13b1, and the organic member 13b2 needs to be immobilized to the circumference of the immobilized aptamer. This ensures immobilization of the aptamer with orientation, thus making it possible to efficiently immobilize a larger amount thereof to the surface of the immobilizing film 13a. In other words, by causing the functional group 13b1 to bind to one end of an aptamer, a binding portion to the detection object which is located at another portion of the aptamer can be oriented upwardly relative to the immobilizing film 13a, thus making it possible to adjacently densely dispose the aptamers.

The aptamer with further improved binding ability to the specific material may have various modifying groups, and is therefore apt, to become hydrophobic and apt to nonspecifically attach to the surface of the immobilizing film 13a without interposing the functional group 13b1 therebetween. Even in this case, by decreasing the surface roughness of the surface of the immobilizing film 13a, or decreasing the amount of oxygen in the surface layer part of the immobilizing film 13a as described above, the organic member 13b2 is capable of uniformly and surely covering the surface of the immobilizing film 13a, thereby effectively suppressing the aptamer from nonspecifically binding to the surface of the immobilizing film 13a.

When immobilizing the reaction part 13b to the surface of the immobilizing film 13a, it is possible to perform the following pretreatment to the surface of the immobilizing film 13a. The following description is made taking, as an example, a structure in which Au is used as the immobilizing film 13a, and $SiO_2$ is used as the insulating member 28.

Firstly, a piranha solution is dropped using a pipette so as to cover at least a portion of the surface of the detection element 3 (immobilizing film 13a) to which the reaction part 13b is immobilized. As the piranha solution, it is necessary to use, for example, one in which 30% hydrogen peroxide solution:sulfuric acid=1:3 (volume ratio). After this is left at room temperature for five minutes, the piranha solution is removed. Consequently, it is possible to remove contaminations (mainly organic matter) existing on the surface of Au as the immobilizing film 13a and the surface of $SiO_2$ as the insulating member 28, and also decrease the surface roughness of Au as the immobilizing film 13a. Additionally, it is possible to impart affinity for the liquid to the surface of $SiO_2$, that is, it is possible to decrease a contact angle of the surface of $SiO_2$ with respect to the specimen liquid. Subsequently, the detection element 3 is washed with ultrapure water, and the detection element 3 is then dried with nitrogen. Instead of the treatment with the piranha solution, for example, UV ozone treatment, ozone water treatment, or oxygen plasma treatment may be employed.

Secondly, an operation to drop ethanol on the surface of the immobilizing film 13a after subjected to the treatment with the piranha solution, or an operation to dip, in ethanol, the immobilizing film 13a after subjected to the treatment with the piranha solution is carried out. Thus, by carrying out the treatment with the piranha solution, an oxide layer formed on the surface of Au as the immobilizing film 13a is removable by reduction reaction of ethanol. The removal of the oxide layer makes it possible to impart non-affinity for the liquid to the surface of Au as the immobilizing film 13a, namely, a contact angle of the surface of Au with respect to the specimen liquid is increased, and also ensures that the amount of oxygen in the surface layer of Au is decreased. Thereafter, the detection element 3 is washed with ultrapure water, and the detection element 3 is then dried with nitrogen.

Thirdly, the foregoing processes are repeated a required number of times as needed.

Fourthly, it is checked whether the surface of Au as the immobilizing film 13a has water repellency. Thereafter, the detection element 3 is washed with ultrapure water, and the detection element 3 is then dried with nitrogen.

After carrying out these processes, the reaction part 13b is immobilized to the surface of Au as the immobilizing film 13a.

Thus, the first IDT electrode 11, the detection part 13, and the second IDT electrode 12 are disposed along the width direction on the upper surface of the detection element 3.

When the first IDT electrode 11, the detection part 13, and the second IDT electrode 12 are taken as one set, the sensor apparatus 100 of the present embodiment has two sets of these as shown in FIG. 3. The single sensor apparatus is capable of detecting two kinds of detection objects by making setting so that the detection object to be detected by the detection part 13 in one set of these is different from the detection object to be detected by the detection part 13 of the other set.

(Detection of Detection Object with Detection Element 3)

When a detection of a specimen liquid is carried out with the detection element 3 using an SAW, firstly, a predetermined voltage is applied from an external measuring device to the first IDT electrode 11 through the wiring line 7 and the first extraction electrode 19, or the like.

Upon this, the surface of the element substrate 10 is excited in the region in which the first IDT electrode 11 is formed, and an SAW having a predetermined frequency is generated. Part of the generated SAW propagates toward the detection part 13 and passes through the detection part 13 and then reaches the second IDT electrode 12.

In the detection part 13, the aptamer (the biomaterial 13b3) of the detection part 13 binds to a specific detection object in a specimen liquid, a weight of the detection part 13 changes according to a quantity of binding. Therefore, a change occurs in characteristics, such as a phase of the SAW passing under the detection part 13. When the SAW whose characteristic is already changed reaches the second IDT electrode 12, a voltage according thereto is to be generated in the second IDT electrode 12. The voltage is then outputted to the outside through the second extraction electrode 20, the wiring line 7, and the like, and the nature and ingredients of the specimen liquid can be examined by reading the voltage with the external measuring device.

The sensor apparatus 100 uses capillary action in order to introduce the specimen liquid into the detection part 13.

To be specific, the flow channel 15 has an elongated tube shape on the lower surface of the second cover member 2 by joining the second cover member 2 to the intermediate cover member 1A as described above. It is therefore possible to cause the elongated tube shaped flow channel 15 to generate capillary action by setting a width or diameter of the flow channel 15 to a predetermined value in consideration of the kind of the specimen liquid and the material of each of the intermediate cover member 1A and the second cover member 2. The width of the flow channel 15 is, for example, 0.5-3 mm, and a depth thereof is, for example, 0.1-0.5 mm. The flow channel 15 includes an upstream portion 15a that is the portion located close to the inlet 14, and a downstream portion (extension portion) 15b that is the portion extending beyond the detection part 13. The exhaust hole 18 being connected to the extension portion 15b is formed in the second cover member 2 (refer to FIG. 2(a)). Upon entrance of the specimen liquid into the flow channel 15, air that is already present in the flow channel 15 is to be released from the exhaust hole 18 to the outside.

By forming the tube that generates capillary action by using the cover member made up of the intermediate cover member 11A and the second cover member 2, upon contact of the specimen liquid with the inlet 14, the specimen liquid is to be sucked into the cover member while flowing through the flow channel 15. Thus, the sensor apparatus 100 includes therein a suction mechanism for the specimen liquid, and is therefore capable of sucking the specimen liquid without using any tool, such as a pipette.

(Affinity for Liquid of Flow Channel 15)

In the sensor apparatus 100 of the present embodiment, all of the inner surface of the flow channel 15, or part of the inner surface, for example, a bottom surface and a wall surface of the flow channel 15 have affinity for liquid. Thus, the inner surface of the flow channel 15 has affinity for liquid, so that capillary phenomenon is apt to occur and the specimen liquid is apt to be sucked from the inlet 14.

In a portion of the inner surface of the flow channel 15 which has affinity for liquid, for example, a contact angle with water needs to set to 60° or less. When the contact angle is 60° or less, capillary phenomenon is more apt to occur. This further ensures the suction of the specimen liquid into the flow channel 15 when the specimen liquid is brought into contact with the inlet 14. This is described in detail below with reference to FIG. 2(a). FIG. 2(a) is a sectional view showing in enlarged dimension a part of the sensor apparatus 100 in FIG. 1(b).

In the present embodiment, setting is made so that a contact angle $\theta 2a$ of a lower surface of a second upstream portion 2ba of the second cover 2 with respect to the specimen liquid, or a contact angle $\theta 1a$ of an upper surface of a first upstream portion 1Aa of the intermediate cover member 1A with respect to the specimen liquid is smaller than a contact angle $\theta 3$ of the detection element 3 (detection part 13) with respect to the specimen liquid. Accordingly, each of the contact angles $\theta 1a$ and $\theta 2a$ of the surfaces of the members located upstream of the detection element 3 in the flow channel 15 for the specimen liquid is smaller than the contact angle $\theta 3$ of the detection element 3 with respect to the specimen liquid. Therefore, the specimen liquid that has entered from the inlet 14 by capillary phenomenon flows smoothly along the surfaces of the members located upstream, thus ensuring that the specimen liquid effectively reaches the detection element 3 (detection part 13).

The contact angle $\theta 2a$ of the lower surface of the second upstream portion 2ba of the second cover 2 with respect to the specimen liquid needs to be set equal to or smaller than the contact angle $\theta 1a$ of the upper surface of the first upstream portion 1Aa of the intermediate cover member 1A with respect to the specimen liquid. With this configuration, the specimen liquid can efficiently be introduced into the detection element 13 by the lower surface of the second upstream portion 2ba of the second cover member 2 and the upper surface of the first upstream portion 1Aa of the intermediate cover member 1A, both of which constitute the flow channel 15. By setting the contact angle $\theta 2a$ to be smaller than the contact angle $\theta 1a$, even in the presence of a clearance between the upper surface of the first upstream portion 1Aa of the intermediate cover member 1A and the detection element 13, the specimen liquid can more efficiently be introduced into the detection element 13 by causing the specimen liquid to flow along the surface of the lower surface of the second upstream portion 2ba of the second cover member 2 extending to the detection part 13.

In the intermediate cover member 1A, a contact angle $\theta 1b$ of the upper surface of the first downstream portion 1Ab with respect to the specimen liquid needs to be set larger than the contact angle $\theta 1a$. This achieves a smoother flow of the specimen liquid on the upstream side of the flow channel 15, on which the detection element 3 (detection part 13) is located, than the downstream side thereof. Additionally, by relatively lowering the flow of the specimen liquid that has reached the detection element 3 (detection part 13), a limited amount of the specimen can be passed at a constant speed for a relatively long time, and the reaction can proceed slowly, leading to measurement with less variation.

In the second cover member 2, the contact angle $\theta 2b$ of the lower surface of a second downstream portion 2bb with respect to the specimen liquid needs to be set larger than the contact angle $\theta 2a$. This achieves a smoother flow of the specimen liquid on the upstream side of the flow channel 15, on which the detection element 3 (detection part 13) is located, than the downstream side thereof. Additionally, by relatively lowering the flow of the specimen liquid that has reached the detection element 3 (detection part 13), the limited amount of the specimen can be passed at the constant speed for the relatively long time, and the reaction can proceed slowly, leading to the measurement with less variation.

In the detection element 3, a contact angle $\theta 3a$ of an upstream region 3a with respect to the specimen liquid needs to be set smaller than a contact angle $\theta 3b$ of a detection region 3b (detection part 13) with respect to the specimen liquid. This causes the specimen liquid to flow smoothly on the upstream side of the detection element 3 (detection part 13) in the flow channel 15, leading to an effective introduction of the specimen liquid to the detection element 3 (detection part 13). Even in the presence of a clearance between the upper surface of the first upstream portion 1Aa of the intermediate cover member 1A and the detection element 13, the specimen liquid can more efficiently be introduced toward the detection element 13 by the lower surface of the second upstream portion 2ba of the second cover member 2 extending to the detection part 13. A contact angle $\theta 3c$ of a downstream region 3c with respect to the specimen liquid needs to be set smaller than a contact angle $\theta 3b$ of the detection region 3b (detection part 13) with respect to the specimen liquid. Consequently, a force to introduce the specimen liquid is relatively strongly exerted on the downstream region 3c than on the detection region 3b (detection part 13). This avoids the fact that the specimen liquid after being subjected to the detection process in the detection element 3 (detection part 13) stays on the detection element 3. It is also possible to relatively decrease or suspend the flow of the specimen liquid after passing through the detection element 3 (detection part 13), thereby suppressing the discharged liquid from leaking outside the sensor apparatus 100. The contact angle $\theta 3a$ is preferably set smaller than the contact angle $\theta 3c$. This achieves a smooth flow of the specimen liquid on the upstream side of the detection element 3 (detection part 13) in the flow channel 15, and the specimen liquid can effectively be introduced into the detection element 13. It is also possible to decrease or suspend the flow of the specimen liquid after passing through the detection element 3 (detection part 13), thereby suppressing the discharged liquid from leaking outside the sensor apparatus 100.

The foregoing contact angle $\theta$ of the surface of each of the components with respect to the specimen liquid is to be measured with the following method.

A water drop is formed on an object surface subjected to measurement of the contact angle $\theta$. Here, water is used instead of the specimen liquid, and a volume of the water drop is 1-4 µl. The measurement is made at room temperature of 25-30° C. and humidity of 40-60% RH.

A shape of the water drop is photographed as an image from a material surface and from a horizontal direction within one minute after forming the water drop.

Subsequently, a contact angle is calculated with tangent method on the basis of the shape of the drop. Here, the vicinity of edge points of a liquid drop (boundary points of the material, the liquid drop, and air) is regarded as a part of a sphere, and a center of the sphere is obtained from a plurality of points on a circular arc. Thus, a tangent of a circle at the edge points of the liquid drop is obtainable. An angle formed by the tangent and the material surface is taken as a contact angle.

When a surface as a measurement object is composed of a single material, a position at which the water drop is formed corresponds to a region including the center of gravity on the assumption that there are uniform mass distribution and thickness distribution. When a material surface as a measurement object is composed of a plurality of materials, a water drop is formed at a region including the center of gravity on the assumption that there are uniform mass distribution and thickness distribution in each of the materials. A contact angle of the material surface in this case is a value obtainable by calculating a weighted average by using an area ratio of each of the materials as a weight.

Alternatively, other measuring method may be employed with which a contact angle is measured by setting a plurality of regions on the material surface. The contact angle of the material surface in this case is a value obtainable by calculating a weighted average by using an area ratio of each of the regions as a weight.

In order to impart affinity for liquid to the inner surface of the flow channel 15, it is possible to employ, for example, a method in which the inner surface of the flow channel 15 is subjected to hydrophillic treatment, a method in which a liquid-affinitive film is attached to the inner surface of the flow channel 15, and a method in which the cover member 2 constituting the flow channel 15 is formed of a liquid-affinitive material. In particular, with the method in which the inner surface of the flow channel 15 is subjected to hydrophillic treatment, or the method in which the liquid-affinitive film is attached to the inner surface of the flow channel 15, the specimen liquid flows through the flow channel 15 along a liquid-affinitive portion. This suppresses the specimen liquid from flowing toward an unintentional location, thereby achieving highly accurate measurement. With each of these methods, even when using a cover member composed of a hydrophobic material, it is possible to cause capillary phenomenon, and hence there is also the advantage of having more choices of materials usable as the cover member.

The method of subjecting the inner surface of the flow channel 15 to hydrophillic treatment may include, for example, changing a functional group of the surface by subjecting the inner surface of the flow channel 15 to oxygen plasma ashing, applying silane coupling agent, followed by applying polyethylene glycol. Besides that, there is also a method in which the inner surface of the flow channel 15 is subjected to surface treatment with a treatment agent including phosphorylcholine.

In the method of attaching the liquid-affinitive film, it is possible to use, as the liquid-affinitive film, a commercially available polyester-based film or polyethylene-based film after being subjected to hydrophillic treatment. The liquid-affinitive film may be attached only to the upper surface, side surface, or lower surface of the flow channel 15, or in any combination of these surfaces.

(Positional Relationship between Flow Channel 15 and Detection Element 3)

In the present embodiment, a depth of the flow channel 15 for the specimen liquid is approximately 0.3 mm, and a thickness of the detection element 3 is approximately 0.3 mm. As shown in FIG. 1(b), the depth of the flow channel 15 and the thickness of the detection element 3 are approximately equal to each other. The flow channel 15 is therefore to be closed by directly mounting the detection element 3 on the flow channel 15. Hence, the element accommodation recess 5 made up of the first cover member 1 configured to mount the detection element 3 thereon and the intermediate cover member 1A to be joined onto the first cover member 1 is disposed in the sensor apparatus 100 as shown in FIGS. 1(b) and 2. The accommodation of the detection element 3 into the element accommodation recess 5 ensures that the flow channel 15 for the specimen liquid is not closed. In other words, the depth of the element accommodation recess 5 is made approximately equal to the thickness of the detection element 3, and the detection element 3 is mounted in the element accommodation recess 5, thereby ensuring the flow channel 15.

From the viewpoint of sufficiently ensuring the flow channel 15 for the specimen liquid, a height of the upper surface of the element substrate 10 from the bottom surface of the element accommodation recess 5 needs to be identical to or smaller than the depth of the element accommodation recess 5 as shown in FIGS. 1(b) and 2. For example, by setting the height of the upper surface of the element substrate 10 from the bottom surface of the element accommodation recess 5 to be equal to the depth of the element accommodation recess 5, the bottom surface of the flow channel 15 and the detection part 13 are capable of having approximately the same height when the interior of the flow channel 15 is viewed from the inlet 14.

A planar shape of the element accommodation recess 5 may be similar to, for example, a planar shape of the element substrate 10. The element accommodation recess 5 needs to be made slightly larger than the element substrate 10. More specifically, the element accommodation recess 5 has such a size that allows formation of a clearance of approximately 200 μm between a side surface of the element substrate 10 and the inner wall of the element accommodation recess 5 when the element substrate 10 is mounted on the element accommodation recess 5.

The detection element 3 is fixed to the bottom surface of the element accommodation recess 5 by a die bond material composed mainly of, for example, an epoxy resin, a polyimide resin, or a silicone resin.

The end portion 19e of the first extraction electrode 19 of the detection element 3 and the wiring line 7 disposed on the upper surface of the first cover member 1 are electrically connected to each other via the thin metallic wire 27 made of, for example, Au. Similarly, the end portion 20e of the second extraction electrode 20 and the wiring line 7 are electrically connected to each other via the thin metallic wire 27. Instead of the thin metallic wire 27, a conductive adhesive material, such as Ag paste, may be used to establish the connection therebetween. A clearance is formed in a connection portion between each of the first extraction electrode 19 and the second extraction electrode 20 and the wiring line 7. Therefore, damage to the thin metallic wire 27 is reducible when the second cover member 2 is stuck to the first cover member 1.

The first extraction electrode 19, the second extraction electrode 20, the thin metallic wire 27, and the wiring line 7 may be covered with the insulating member 28 as described above. This makes it possible to suppress corrosion of these electrodes and the like.

Thus, by accommodating the detection element 3 into the element accommodation recess 5 made up of the first cover member 1 and the intermediate cover member 1A, the sensor apparatus 100 ensures the flow channel 15 extending from the inlet 14 to the detection part 13, thereby allowing the specimen liquid sucked up from the inlet 14 by capillary action or the like to flow into the detection part 13. That is, the present embodiment is capable of providing the sensor apparatus 100 that includes therein the suction mechanism while employing the thick detection element 3.

The foregoing sensor apparatus 100 is manufacturable, for example, in the following manner.

Firstly, the first cover member 1 including the terminal 6 and the wiring line 7 formed thereon is prepared as shown in FIG. 7(a).

Subsequently, the intermediate cover member 1A is laminated on the first cover member 1 as shown in FIG. 7(b). Here, the intermediate cover member 1A is made up of the first upstream portion 1Aa and the first downstream portion 1Ab.

Subsequently, the detection element 3 is mounted between the first upstream portion 1Aa and the first downstream portion 1Ab of the intermediate cover member 1A by using the thin metallic wire 27 as shown in FIG. 7(c). Either of the process of mounting the intermediate cover member 1A on the first cover member 1, and the process of mounting the detection element 3 on the first cover member 1 may be carried out first.

Subsequently, the third substrate 2a of the second cover member 2 is laminated on the intermediate cover member 1A as shown in FIG. 7(d).

Then, the fourth substrate 2b is laminated on the third substrate 2a, thereby manufacturing the sensor apparatus 100 of the present embodiment as shown in FIG. 7(e).

In the manufacturing of the sensor apparatus 100 of the present embodiment, the manufacturing of the detection element 3 includes the following steps (i) to (iii):

(i) forming the first IDT electrode 11, the second IDT electrode 12, the first extraction electrode 19, and the second extraction electrode 20 by performing resist patterning and then lift-off;

(ii) forming the insulating member 28 by forming a film and then patterning; and (iii) forming the immobilizing film 13a, the end portion 19e of the first extraction electrode 19, and the end portion 20e of the second extraction electrode 20.

A modification of the sensor apparatus 100 according to the first embodiment is described below.

<Modification>

Figure 8A:
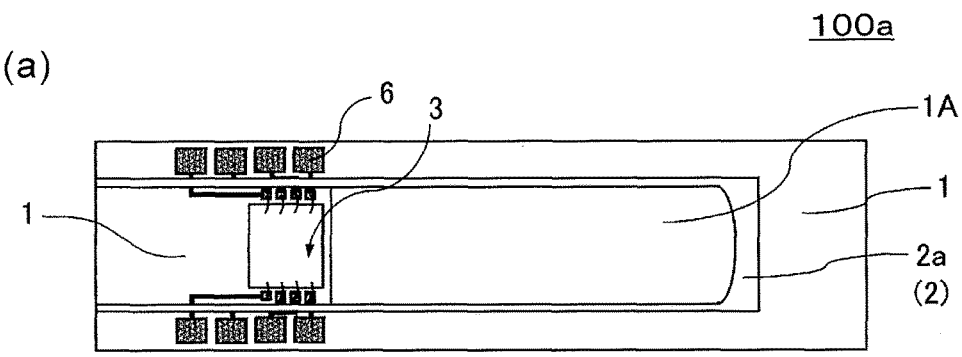
FIG. 8 is plan views respectively showing modifications of the sensor apparatus in FIG. 1, specifically, FIGS. 8(a) and 8(b) correspond to FIG. 7(d), and FIG. 8(c) corresponds to FIG. 1(a)
Figure 8B:
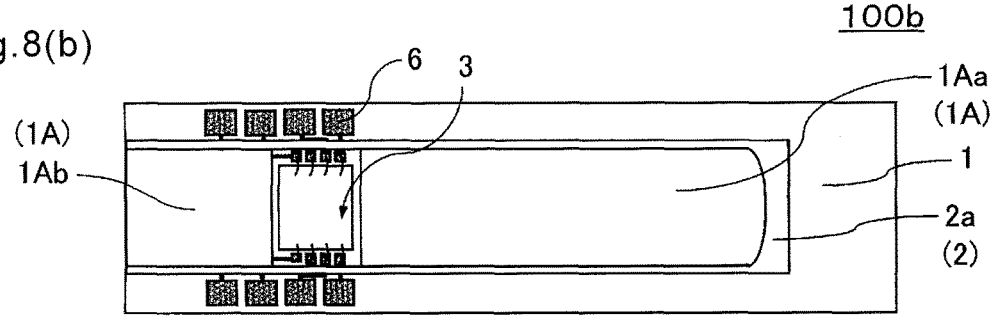
Figure 8C:
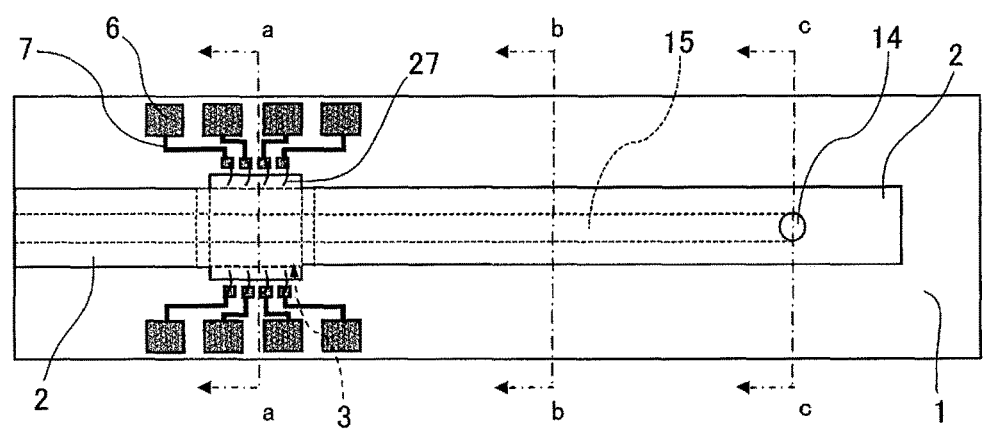

FIG. 8 is plan views respectively showing sensor apparatuses 100a, 100b, and 100c according to modifications of the sensor apparatus 100 in FIG. 1. Specifically, FIGS. 8(a) and 8(b) correspond to FIG. 7(d), and FIG. 8(c) corresponds to FIG. 1(a).

The sensor apparatuses 100a and 100b of the present modifications are different from the sensor apparatus 100 of the foregoing first embodiment in that the width of each of the intermediate cover member 1A and the second cover member 2 is larger than the width of the detection element 3. In the sensor apparatus 100a, the intermediate cover member 1A (first downstream portion 1Ab) is not disposed on the first cover member 1 in the downstream of the detection element 3 as shown in FIG. 8(a). In contrast to this, the sensor apparatus 100b, the intermediate cover member 1A (first downstream portion 1Ab) is disposed on the first cover member 1 in the downstream of the detection element 3 as shown in FIG. 8(b).

The sensor apparatus 100c of the present modification is different from the sensor apparatus 100 of the foregoing first embodiment in disposition of the terminals 6 with respect to the detection element 3.

To be specific, in the sensor apparatus 100, the terminals 6 are located closer to the exhaust hole 18 than an end portion of the detection element 3 which is close to the inlet 14 as shown in FIG. 1. In contrast to this, in the sensor apparatus 100c of the present embodiment, at least part of the terminals 6 is located closer to the inlet 14 than an end portion of the detection element 3 which is close to the inlet 14.

In the four terminals 6 disposed on one side of the detection element 3 with respect to the longitudinal direction of the flow channel 15, the wiring lines 7 respectively connected to the outer two terminals 6 have approximately the same length, and the wiring lines 7 respectively connected to the inner two terminals 6 have approximately the same length. This makes it possible to avoid that signals obtainable by the detection element 3 vary depending on the length of the wiring line 7. Additionally, for example, one pair of the wiring lines 7 having approximately the same length are connected to a portion of the detection part 13 of the detection element 3 which is for detecting the detection object, and another pair of wiring lines 7 having approximately the same length are connected to a reference electrode with respect to the detection object in the detection part 13 of the detection element 3. This configuration can reduce the foregoing variations of the signals and improves detection reliability.

FIG. 9(a) is a plan view of a sensor apparatus 101 according to a modification of the sensor apparatus 100 in FIG. 1, FIG. 9(b) is a sectional view thereof taken along a length direction, and FIG. 9(c) is a sectional view thereof taken along a width direction.

The sensor apparatus 101 of the present embodiment is different from the sensor apparatus 100 of the foregoing first embodiment in that a filling member 9 is disposed in the clearance between the detection element 3 and the intermediate cover member 1A.

The filling member 9 can be configured so as to include a material different from that of the intermediate member 1A and the element substrate 10. For example, a resin material, such as PDMS (polydimethylsiloxane), is usable. The filling member 9 need not be disposed in all region of the clearance between the detection element 3 and the intermediate cover member 1A. For example, the filling member 9 may be disposed only on a portion corresponding to the flow channel 15. With the sensor apparatus 101 of the present modification, the filling member 9 is located at the clearance between the detection element 3 and the intermediate member 1A. It is therefore possible to suppress inhibition of capillary phenomenon due to the clearance, thus leading to a smoother suction of the specimen liquid toward the detection element 3.

FIG. 10 is a plan view showing a manufacturing process of the sensor apparatus 101 in FIG. 9.

Similarly to the sensor apparatus 100 of the foregoing first embodiment, the first step includes laminating the intermediate cover member 1a on the first cover member 1 including the terminal 6 and the wiring line 7 formed thereof, and mounting the detection element 3 thereon by using the thin metallic wire 27 as shown in FIGS. 10(a) to 10(c).

The subsequent step includes disposing the filling member 9 in the clearance between the detection element 3 and the intermediate cover member 1A as shown in FIG. 10(d).

Similarly to the sensor apparatus 100 of the foregoing first embodiment, the sensor apparatus 101 of the present embodiment is manufactured by laminating the third substrate 2a of the second cover member 2 on the intermediate, and laminating the fourth substrate 2b on the third substrate 2a as shown in FIGS. 10(e) and 10(f).

FIG. 11 is a diagram showing the sensor apparatus 101a according to a modification of the sensor apparatus 100 in FIG. 1, specifically showing a manufacturing process thereof.

The sensor apparatus 101a of the present modification is different from the sensor apparatus 100 of the foregoing first embodiment in that the entire periphery of the detection element 3 is surrounded by a tabular frame shaped intermediate cover member 1A in a top perspective (top view) in which the sensor apparatus 100a is seen through from the upper surface of the second cover member 2. The filling member 9 is located in the clearance between the detection element 3 and the intermediate cover member 1A so as to surround an outer periphery of the detection element 3 as shown in FIGS. 11(d) and 11(e). This contributes to reducing a difference in level or gap between the detection element 3 and the circumference thereof in the flow channel 15, thus leading to a smooth flow of the specimen liquid onto the detection element 3. The filling member 9 is capable of covering a part of the wiring line 7, and the thin metallic wire 27 connecting the detection element 3 and the wiring line 7 in a region between the detection element 3 and the terminals 6. It is therefore possible to suppress deterioration of detection sensitivity due to contacts between these and the specimen liquid.

In the present modification, after forming the intermediate cover member 1A and the detection element 3 as shown in FIG. 11(b), the detection element 3 and the wiring line 7 are connected to each other via the thin metallic wire 27 as shown in FIG. 11(c). Instead of this, the intermediate cover member 1A may be formed after forming the detection element 3 and connecting the detection element 3 and the wiring line 7 via the thin metallic wire 27.

FIG. 12 is a plan view showing the sensor apparatuses 101b and 101c respectively according to modifications of the sensor apparatus 100 in FIG. 1, and corresponds to FIG. 7(d).

Figure 12A:
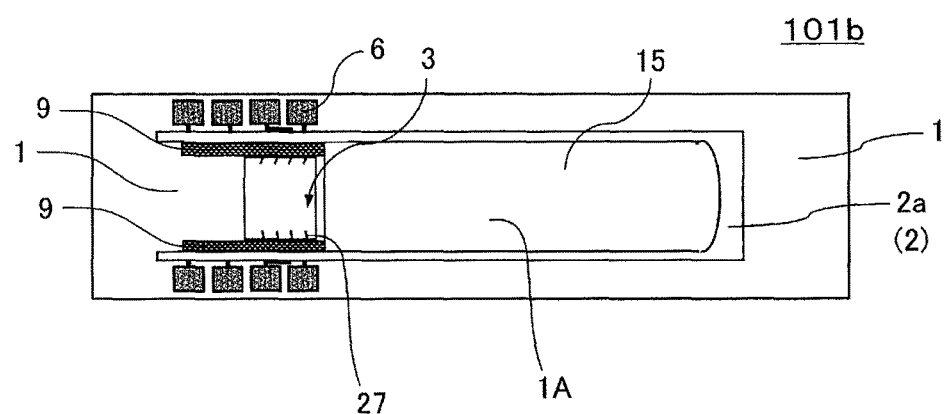
FIG. 12 is a plan view showing a modification of the sensor apparatus in FIG. 1, which corresponds to FIG. 7(d)
Figure 12B:
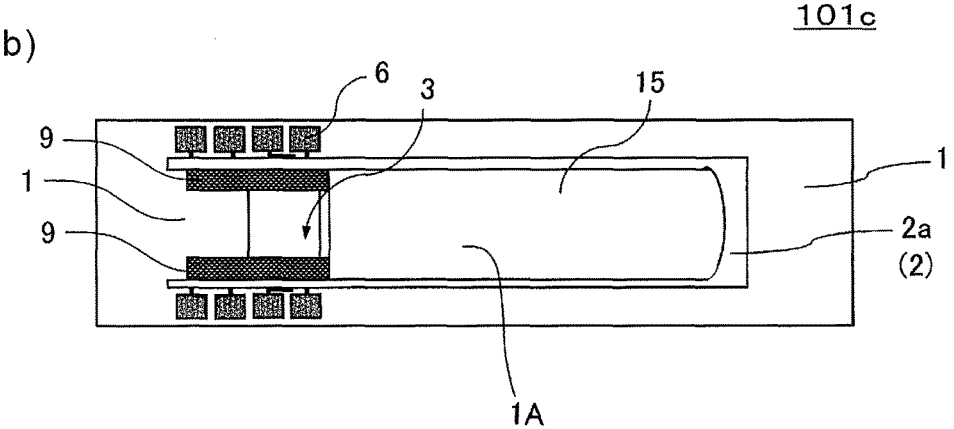

The sensor apparatuses 101b and 101c of the present modifications are different from the sensor apparatus 100 of the foregoing first embodiment in that the filling member 9 is located along the longitudinal direction of the flow channel 15 in the clearance between the detection element 3 and the intermediate cover member 1A as shown in FIGS. 12(a) and 12(b). This contributes to reducing a difference in level between the detection element 3 and both sides thereof, or a gap therebetween, thereby causing the specimen liquid to also flow smoothly to the detection element 3 from the side thereof. Additionally, the filling member 9 is capable of covering the part of the wiring line 7, and the thin metallic wire 27 connecting the detection element 3 and the wiring line 7 in the region between the detection element 3 and the terminals 6. It is therefore possible to suppress deterioration of detection sensitivity due to contacts between these and the specimen liquid.

Alternatively, the filling member 9 may cover not only the clearance between the detection element 3 and the intermediate cover member 1A, but also a portion of the thin metallic wire 27 for connecting the detection element 3 and the wiring line 7 which is located on the upper surface of the detection element 3 (element substrate 10) as shown in FIG. 12(b). This contributes to further reducing sensitivity deterioration due to a contact between the thin metallic wire 27 and the specimen liquid.

A configuration in a sensor apparatus according to each of embodiments described later is directly applicable to, or applicable in a form suitable for the foregoing configurations to the sensor apparatus 100 according to the first embodiment and the sensor apparatuses respectively according to the modifications thereof.

Second Embodiment

Figure 13:
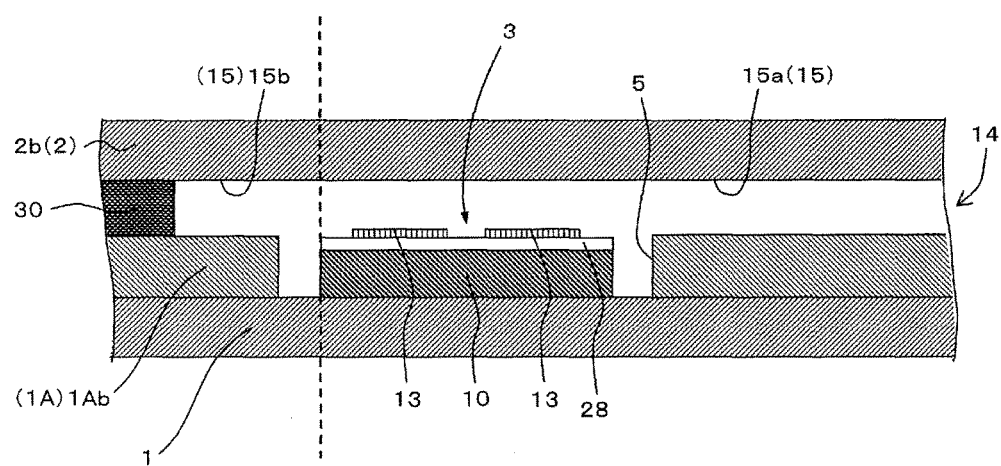
FIG. 13 is a diagram showing a sensor apparatus according to a second embodiment of the present invention, which corresponds to FIG. 2(a)

FIG. 13 is a diagram showing a sensor apparatus 200 according to a second embodiment of the present invention, and corresponds to FIG. 2(a).

In the sensor apparatus 200 of the present embodiment, a liquid absorbing material 30 that absorbs a specimen liquid at a predetermined speed is disposed at a terminal portion of the flow channel 15 on the upper surface of the first downstream portion 1Ab of the intermediate cover member 1A. Therefore, by absorbing an excessive specimen liquid, the amount of the specimen liquid flowing on the detection part 13 can be made constant to achieve highly stable measurement. As the liquid absorbing material 30, a porous material capable of absorbing liquid, such as a sponge, is usable. It is preferable to use, for example, nitrocellulose.

Also in the sensor apparatus 200 of the present embodiment, the detection element 3 and the intermediate cover member 1A that constitutes at least a part of the flow channel 15 are disposed together as in the sensor apparatus 100 of the foregoing first embodiment. Therefore, even when using the thick detection element 3, the flow channel 15 for the specimen liquid extending from the inlet 14 to the detection part 13 can be ensured, and the specimen liquid sucked from the inlet 14 by capillary phenomenon or the like can be flown to the detection part 13. In other words, it is possible to provide the sensor apparatus 200 to simplify a measurement operation which includes therein a suction mechanism for the specimen liquid while using the thick detection element 3. In the flow channel 15 for the specimen liquid, each of contact angles θ1a and θ2a of a surfaces of members located upstream of the detection element 3 with respect to the specimen liquid is smaller than a contact angle θ3 of the surface of the detection element 3 (detection part 13) with respect to the specimen liquid. This achieves a smooth flow of the specimen liquid that has entered from the inlet 14 toward the detection element 3 (detection part 13) through the surface of the member located upstream.

In the present embodiment, a contact angle θ1b of the upper surface of the first downstream portion 1Ab of the intermediate cover member 1A with respect to the specimen liquid may be set larger than the contact angle θ3. This makes it possible to control speed at which the specimen liquid passing through the detection element 3 (detection part 13) is absorbed by the liquid absorbing material 30. It is consequently possible to improve detection stability by controlling the specimen liquid in the detection element 3 (detection part 13) to a predetermined amount.

Figure 14A:
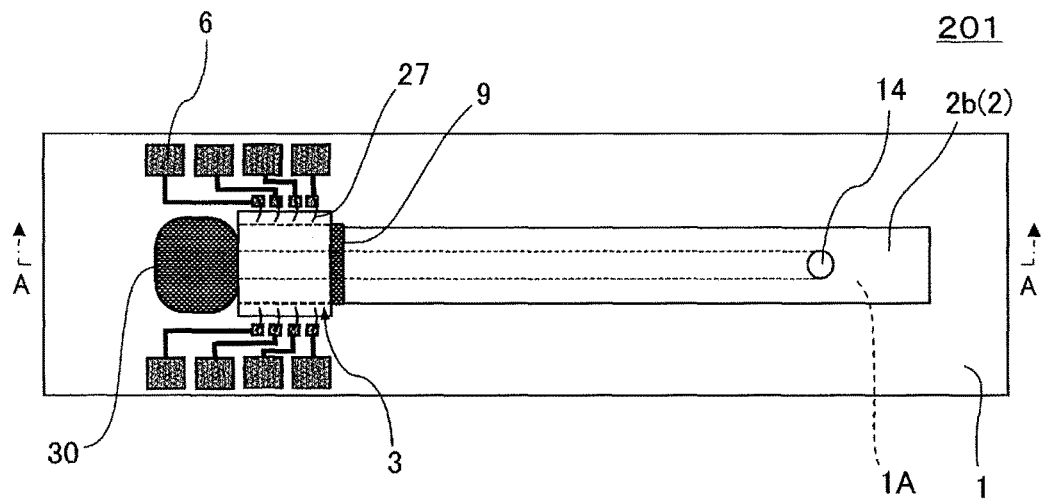
FIG. 14(a) is a plan view showing a modification of the sensor apparatus in FIG. 13.
Figure 14B:
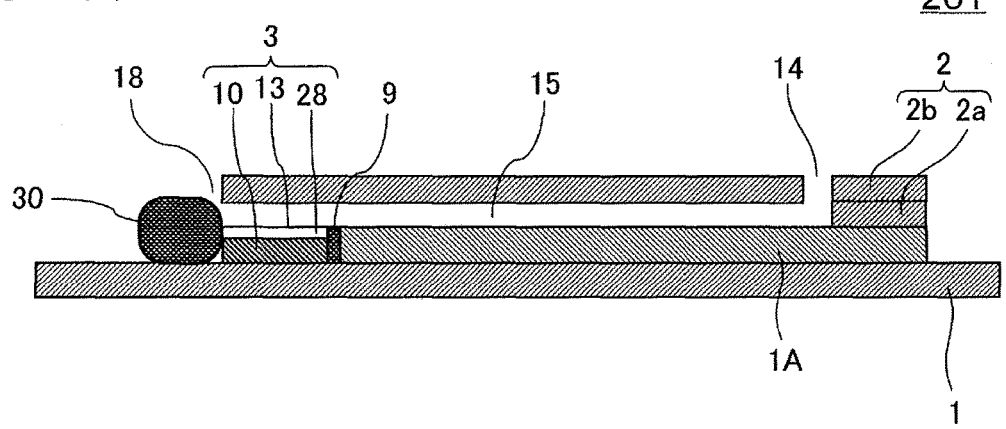
FIG. 14(b) is a sectional view thereof taken along a length direction, specifically a sectional view taken along line A-A in FIG. 14(a)

FIG. 14 is a diagram showing a sensor apparatus 201 according to a modification of the sensor apparatus 200 in FIG. 13. Specifically, FIG. 14(a) is a plan view thereof, and FIG. 14(b) is a sectional view taken along a length direction.

Instead of the first downstream portion 1Ab of the intermediate cover member 1A in the sensor apparatus 100 of the foregoing first embodiment, the sensor 201 of the present modification includes the liquid absorbing material 30 located opposite to the intermediate cover member 1A with respect to the detection element 3 on the upper surface of the first cover member 1. Also in the present modification, by absorbing an excessive specimen liquid, the amount of the specimen liquid flowing on the detection part 13 can be made constant to achieve highly stable measurement.

In the present modification, the liquid absorbing material 30 is disposed away from the terminal portion of the flow channel 15 with a slight clearance interposed therebetween. Thus, the clearance functions as an exhaust hole 18, thereby making it possible to effectively produce capillary phenomenon.

Figure 15A:
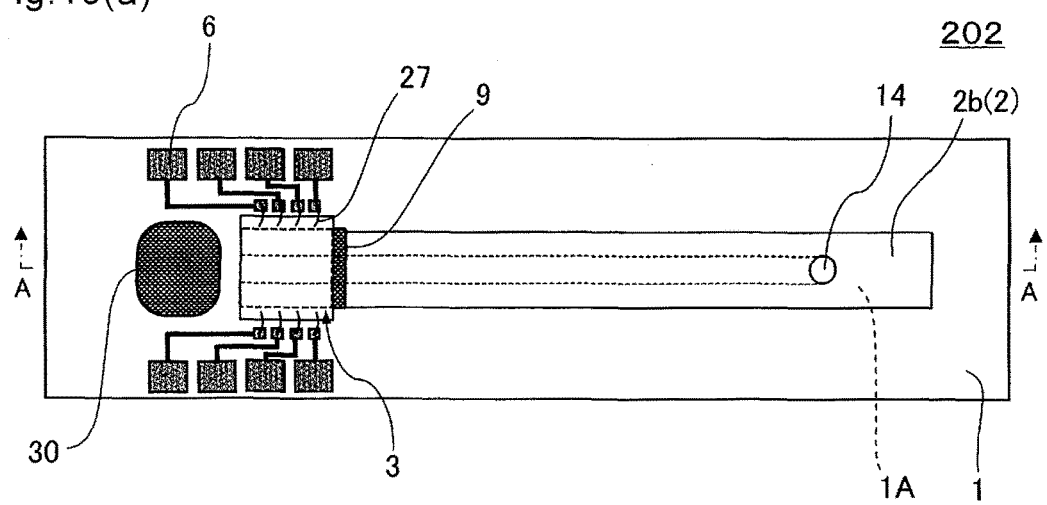
FIG. 15(a) is a plan view showing a modification of the sensor apparatus in FIG. 13.
Figure 15B:
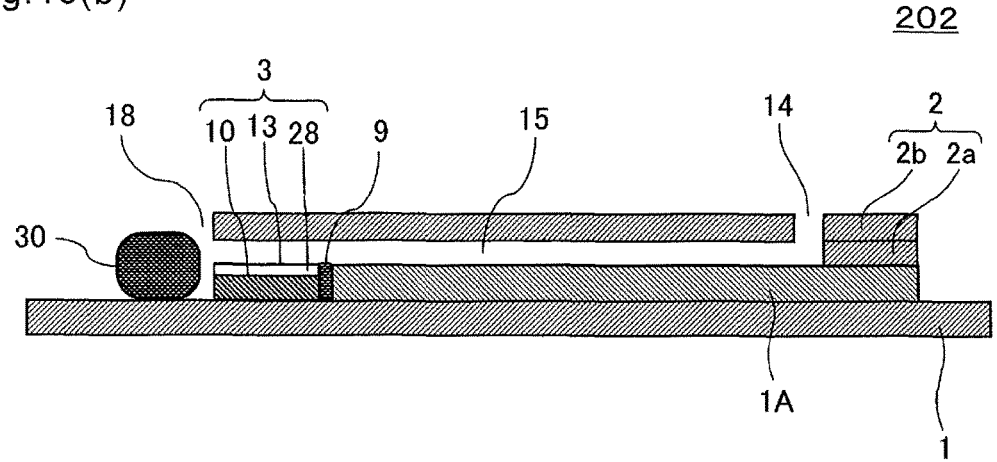
FIG. 15(b) is a sectional view thereof taken along a length direction, specifically a sectional view taken along line A-A in FIG. 15(a)

FIG. 15 is a diagram showing a sensor apparatus 202 according to a modification of the sensor apparatus 200 in FIG. 13. Specifically, FIG. 15(a) is a plan view thereof, and FIG. 15(b) is a sectional view taken along a length direction.

The sensor apparatus 202 of the present modification is different from the sensor apparatus 201 shown in FIG. 14 in that the liquid absorbing material 30 is disposed away from the detection element 3 with a clearance interposed therebetween on the opposite side of the intermediate cover member 1A with respect to the detection element 3 on the upper surface of the first cover member 1 as shown in FIG. 15. With this configuration, the specimen liquid flowing through the flow channel 15 passes through the upper surface of the detection element 3 and is then absorbed by the liquid absorbing material 30. It is therefore possible to absorb the specimen liquid after contributing to a detection on the upper surface of the detection element 3.

FIG. 16 is sectional views respectively taken along a length direction of sensor apparatuses 203 and 204 according to modifications of the sensor apparatus 200 in FIG. 13.

Figure 16A:
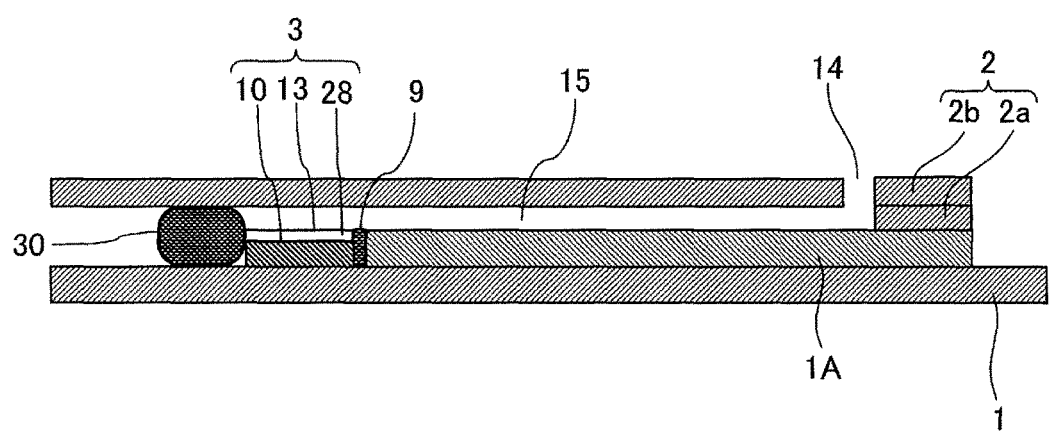
FIG. 16 is a diagram showing a modification of the sensor apparatus in FIG. 13, specifically a sectional view taken along a length direction.
Figure 16B:
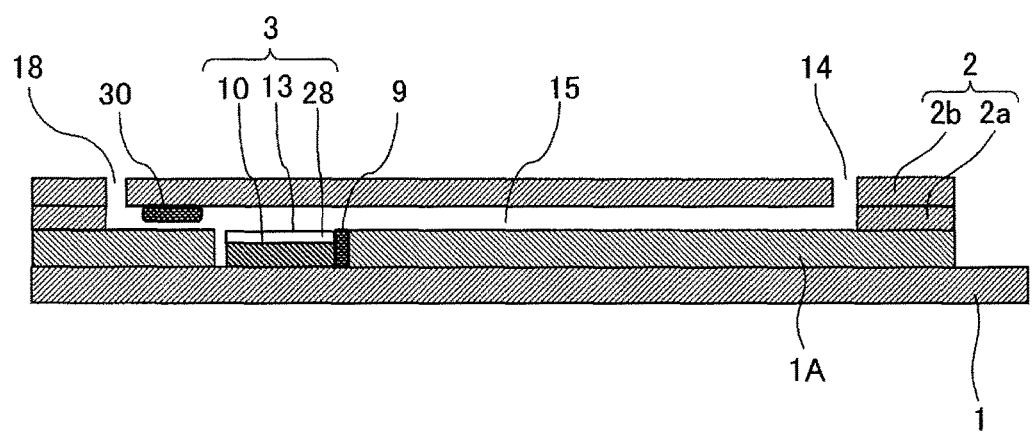

The sensor apparatus 203 of the present modification is different from the sensor apparatus 201 shown in FIG. 14 in that the liquid absorbing material 30 is in contact with both of the upper surface of the first cover member 1 and the lower surface of the second cover member 2, namely, the upper and lower surfaces of the flow channel 15 as shown in FIG. 16(a). Therefore, by absorbing an excessive specimen liquid, the amount of the specimen liquid flowing on the detection part 13 can be made constant to achieve highly stable measurement as described above.

Additionally in the present modification, it is possible to cause the porous liquid absorbing material 30 to function as the exhaust hole 18 by controlling porosity of the liquid absorbing material 30. On that occasion, the liquid absorbing material 30 can be disposed so as to close the flow channel 15 by being brought into contact not only with the upper and lower surfaces of the flow channel 15 but also a side wall of the flow channel 15 as described above.

The sensor apparatus 204 according to other modification is different from the sensor apparatus 201 shown in FIG. 14 in that the liquid absorbing material 30 is in contact only with the lower surface of the second cover member 2 as shown in FIG. 16(b). Thus, the liquid absorbing material 30 produces the action of sucking the specimen liquid because of the contact with the specimen liquid flowing through the flow channel 15, thereby making it possible to effectively introduce the specimen liquid onto the upper surface of the detection element 3 located at the front in a flow direction.

The sensor apparatus 204 is different from the sensor apparatus 100 of the first embodiment in that the fourth substrate 2b is provided with an exhaust hole 18 extending through the fourth substrate 2b in a thickness direction thereof. The exhaust hole 18 is disposed at a position to make connection with an end portion of the flow channel 15.

The present invention may be practiced in various forms without being limited to the foregoing embodiments.

For example, though in the foregoing embodiments, the description has been made of ones in which the detection element 3 is composed of the surface acoustic wave element, the detection element 3 is not limited thereto. For example, a detection element 3 may be used which is provided with an optical waveguide so as to cause surface plasmon resonance. In this case, for example, a change in optical refraction index in the detection part is to be measured. Besides that, it is possible to use the detection element 3 having an oscillator formed on a piezoelectric substrate of quartz or the like. In this case, for example, a change in oscillation frequency of the oscillator is to be measured.

As the detection element 3, a plurality of kinds of devices may be disposed together on a single substrate. For example, an oxygen electrode for oxygen electrode method may be disposed adjacent to the SAW element. In this case, measurement with oxygen method is also executable besides immunization method using an antibody and an aptamer, thereby increasing the number of inspectable items at once.

Although in the foregoing embodiments, the description has been made of the cases where the single detection element 3 is disposed, a plurality of the detection elements 3 may be disposed. In this case, the element accommodation recess 5 may be disposed for each of the detection elements 3. Alternatively, an element accommodation recess 5 having an enough length or width to accommodate all the detection elements 3 may be formed.

Although the foregoing embodiments have exemplified the case where the first cover member 1, the intermediate cover member 1A, and the second cover member 2 are separate members, without limitation thereto, it is possible to use one in which any two or all of these members are integrated with one another.

For example, the configuration of the modification of the sensor apparatus 100 in the first embodiment may be applied to the configuration of the sensor apparatus 200 in the second embodiment. In other words, the modifications and the forms of individual components related to the sensor apparatus in the foregoing embodiments are applicable to a sensor apparatus of other embodiment without departing from the technical idea of the present invention. For example, the sensor apparatus may be configured so that the surface roughness of the immobilizing film 13a is smaller than the surface roughness of the element electrode 29, the amount of oxygen in the surface layer part of the immobilizing film 13a is smaller than the amount of oxygen in the surface layer part of the element electrode 29, and the insulating member 28 is not included. This makes it possible to detect the detection object with satisfactory sensitivity and satisfactory accuracy for the reason as described in the foregoing embodiments. This also makes it possible to omit the process of forming the insulating member 28, thus reducing manufacturing costs for the sensor apparatus.

For example, the foregoing embodiments have described the case where the specimen is in the liquid state (specimen liquid), without limitation thereto. That is, the specimen is not limited to be in the liquid state as long as being measurable with the sensor apparatus of the present embodiments. For example, the specimen may be in a gel state or a gas state. The specimen may be one whose state changes, such as one which approaches a solid state from the liquid state in the flow channel 15 (on the detection part 13a).

DESCRIPTION OF THE REFERENCE NUMERAL

1: first cover member
1A: intermediate cover member
   1Aa: first upstream portion
      $\theta 1a$: contact angle
   1Ab: first downstream portion
      $\theta 1b$: contact angle
2: second cover member
   2a: third substrate
   2b: fourth substrate
      2ba: second upstream portion
         $\theta 2a$: contact angle
      2bb: second downstream portion
         $\theta 2b$: contact angle
3: detection element
   3a: upstream region
      $\theta 3a$: contact angle
   3b: detection region (detection part)
      $\theta 3b$: contact angle
   3c: downstream region
      $\theta 3c$: contact angle
4: recess forming portion
5: element accommodation recess
6: terminal
7: wiring line
9: filling member
10: element substrate
11: first IDT electrode
12: second IDT electrode
13 (3b): detection part
   13a: immobilizing film
   13b: reaction part
      13b1: functional group
      13b2: organic member
      13b3: biomaterial
14: inlet
15: flow channel
   15a: upstream portion
   15b: downstream portion (extension portion)
18: exhaust hole
19: first extraction electrode
   19e: end portion (pad portion)
20: second extraction electrode
   20e: end portion (pad portion)
27: conducting wire (thin metallic wire)
28: insulating member
   28a: covered portion
   28b: outer peripheral portion
29: element electrode
30: liquid absorbing material
100: sensor apparatus

The invention claimed is:

1. A sensor apparatus, comprising:
an element substrate;
an element electrode located on an upper surface of the element substrate;
an insulating member covering at least a part of the element electrode; and
a detection part comprising an immobilizing film located on the upper surface of the element substrate or an upper surface of the insulating member, and configured to detect a detection object contained in a specimen,
wherein a surface roughness of the immobilizing film is smaller than a surface roughness of the element electrode.

2. The sensor apparatus according to claim 1,
wherein the element electrode comprises
a first IDT (Interdigital Transducer) electrode configured to generate an acoustic wave, and
a second IDT electrode configured to receive the acoustic wave to be propagated from the first IDT electrode, and wherein the surface roughness of the immobilizing film is smaller than a surface roughness of each of the first IDT electrode and the second IDT electrode.

3. A sensor apparatus according to claim 2, wherein the immobilizing film is located between the first IDT electrode and the second IDT electrode in a top perspective.

4. The sensor apparatus according to claim 1, wherein an amount of oxygen in a surface layer part of the immobilizing film is smaller than an amount of oxygen in a surface layer part of the element electrode.

5. The sensor apparatus according to claim 1, wherein the detection part further comprises a reaction part located on an upper surface of the immobilizing film, and configured to cause a chemical reaction with the detection object contained in the specimen.

6. The sensor apparatus according to claim 5, wherein the reaction part comprises a thiol group being bound to the upper surface of the immobilizing film.

7. The sensor apparatus according to claim 6, wherein the reaction part further comprises an organic member being bound to the thiol group.

8. The sensor apparatus according to claim 1, wherein the reaction part further comprises a biomaterial being immobilized above the immobilizing film, and containing at least one kind selected from among peptide, protein, and nucleic acid.

9. The sensor apparatus according to claim 1, wherein the immobilizing film comprises a same material as the element electrode.

10. The sensor apparatus according to claim 1, wherein the element electrode comprises a plurality of layers, and an uppermost layer of the plurality of layers comprises a different material from the immobilizing film.

11. The sensor apparatus according to claim 1, wherein the element electrode and the immobilizing film comprise Au.

12. The sensor apparatus according to claim 1, wherein a thickness of the immobilizing film is smaller than a thickness of the element electrode.

13. The sensor apparatus according to claim 1, wherein the insulating member comprises a covered portion covered by the immobilization film and an outer peripheral portion surrounding the covered portion, wherein a top surface of the outer peripheral portion is lower than a top surface of the covered portion in a cross-sectional view.

14. The sensor apparatus according to claim 1, wherein the insulating member comprises $SiO_2$.

* * * * *